United States Patent
Roncucci et al.

(10) Patent No.: US 12,138,309 B2
(45) Date of Patent: Nov. 12, 2024

(54) TOPICAL FORMULATIONS CONTAINING PHTHALOCYANINE PHOTOSENSITIZERS

(71) Applicant: MOLTENI THERAPEUTICS S.R.L., Scandicci (IT)

(72) Inventors: Gabrio Roncucci, Poggibonsi (IT); Lia Fantetti, Florence (IT); Annalisa Cocchi, Poggio a Caiano (IT); Moira Municchi, Florence (IT); Francesco Giuliani, Siena (IT); Silvia Tampucci, Pisa (IT); Daniela Monti, Camaiore (IT); Giacomo Chiti, Prato (IT)

(73) Assignee: MOLTENI THERAPEUTICS S.R.L., Scandicci (IT)

( * ) Notice: Subject to any disclaimer, the term of this patent is extended or adjusted under 35 U.S.C. 154(b) by 684 days.

(21) Appl. No.: 17/435,915

(22) PCT Filed: Mar. 6, 2020

(86) PCT No.: PCT/IB2020/051945
§ 371 (c)(1),
(2) Date: Sep. 2, 2021

(87) PCT Pub. No.: WO2020/178791
PCT Pub. Date: Sep. 10, 2020

(65) Prior Publication Data
US 2022/0233696 A1 Jul. 28, 2022

(30) Foreign Application Priority Data
Mar. 6, 2019 (IT) .................. 102019000003247

(51) Int. Cl.
*A61K 41/00* (2020.01)
*A61K 9/00* (2006.01)
*A61K 47/10* (2017.01)
*A61K 47/38* (2006.01)
*A61P 17/02* (2006.01)
*A61P 31/02* (2006.01)

(52) U.S. Cl.
CPC ........ *A61K 41/0071* (2013.01); *A61K 9/0014* (2013.01); *A61K 47/10* (2013.01); *A61K 47/38* (2013.01); *A61P 17/02* (2018.01); *A61P 31/02* (2018.01)

(58) Field of Classification Search
CPC .............................................. A61K 41/0071
See application file for complete search history.

(56) References Cited

U.S. PATENT DOCUMENTS 5,965,598 A * 10/1999 Roncucci ........... A61K 41/0071
514/183
8,664,382 B2 * 3/2014 Roncucci ................ A61P 31/00
544/185

FOREIGN PATENT DOCUMENTS

| CN | 1649584 A | 8/2005 |
|----|-----------|--------|
| EP | 1356813 A1 | 10/2003 |
| WO | 03090744 A1 | 11/2003 |

OTHER PUBLICATIONS

Fabin and Touitou, "Localization of Lipophilic Molecules Penetrating Rat Skin In Vivo by Quantitative Autoradiography," International Journal of Pharmaceutics, 74:59-65 (1991).
Fabris, C., et al., "A Novel Tetracationic Phthalocyanine as a Potential Skin Phototherapeutic Agent," Experimental Dermatology, 14:675-683 (2005).
Chinese Office Action for Application No. P020736CN-01, dated Nov. 30, 2022.
International Search Report for PCT/IB2020/051945, dated Jun. 24, 2020.
Simonetti, O., et al., "Effectiveness of Antimicrobial Photodynamic Therapy with a Single Treatment of RLP068/CI in an Experimental Model of *Staphylococcus aureus* Wound Infection," British Journal of Dermatology, 164(5):987-995 (2011).
Written Opinion for PCT/IB2020/051945, dated Jun. 24, 2020.

* cited by examiner

*Primary Examiner* — Golam M Shameem
(74) *Attorney, Agent, or Firm* — Troutman Pepper Hamilton Sanders LLP

(57) ABSTRACT

The present invention describes topical formulations for use in photodynamic therapy (PDT) of skin affections, said formulations comprising a Zn-phthalocyanine derivative.

12 Claims, 14 Drawing Sheets

TOPICAL FORMULATIONS CONTAINING PHTHALOCYANINE PHOTOSENSITIZERS

CROSS-REFERENCE TO RELATED APPLICATIONS

This application is a national stage application under 35 U.S.C. § 371 of PCT Application No. PCT/162020/051945, filed Mar. 6, 2020, which claims the priority benefit of Italy Patent Application No. 102019000003247, filed Mar. 6, 2019, which are hereby incorporated by reference in their entirety.

FIELD OF THE INVENTION

The present invention refers to the field of formulations, suitable for topical administration, containing phthalocyanine photosensitizers. In particular, it refers to formulations containing Zn-phthalocyanine derivatives useful for the local therapy of localized skin and mucosal affections, also of microbial origin.

STATE OF THE ART

It is known that molecules containing the phthalocyanine chromofluorophore macrocycle produce reactive oxygen species (ROS), such as radicals or singlet oxygen, following the absorption of light radiation and, in particular of visible light. Due to their properties, the phthalocyanine compounds can be excited by radiations capable of penetrating the tissues and therefore guaranteeing the in situ production of ROS, not only in the superficial layers of the skin or mucosa, thus allowing the treatment of pathologies that are not exclusively superficial and have been proposed for some time in photodynamic therapy (hereinafter indicated by the abbreviation "PDT") for the purpose of therapeutic treatment and also for diagnostic purposes.

Examples of such compounds are described by Ogura et al. *Journal of Porphyrins and Phthalocyanines* 2006, 10, 1116-1124.

Photosensitizing agents useful in PDT are, for example, the zinc phthalocyanine complexes and the conjugates thereof described in the patent EP 906 758, in the name of the Applicant.

Furthermore, in EP 1 444 236 and EP 1 883 640 (both in the name of the Applicant) a process for the separation of regioisomeric mixtures and a process for the preparation of chlorides of phthalocyanine complexes are respectively described.

The compounds described and obtained according to the above reported processes have proven to be effective photosensitizing agents in the PDT treatment for the inactivation of tumour cells, and therefore with a potential use as anticancer agents, in the cancerous or precancerous affections of districts that can be reached by light, as well as pathogens capable of supporting microbial infections: in particular the product [1,8(11),15(18),22(25)-tetrakis-(3-N,N,N-trimethylammoniophenoxy)] Zinc phthalocyaninate tetrachloride (RLP068), corresponding to example 53 of EP 906 758, has proved to be particularly active and endowed with useful features for industrial development. The document WO2011/012698 (also in the name of the Applicant) describes a chromatographic purification method of the aforesaid product, necessary for proposing the product at an adequate purity for clinical use, through a feasible and scalable procedure at a standard industrial production level.

The aforesaid phthalocyanine molecules have a complex macrocyclic structure in which the presence of zinc as a metal coordinated by the macrocycle and the hydrophilic peripheral substituents (of a cationic nature) present on the macrocycle contribute to the amphiphilic nature, ultimately due to the presence of a substantially hydrophobic central core and of a series of peripheral hydrophilic substituents.

The formulation with zinc phthalocyanine photosensitizing agents, due to the amphiphilic nature of the aforesaid molecules, is known to be problematic, in such a way that mixtures of the complex with many solubilizing agents do not show significant skin penetration or tend to form aggregates by virtue of the planar structure in the form of complexes (Lenznoff C. C. et al., *Photochem. Photobiol.* 49, 279 (1989)). The latter phenomenon causes the loss of the photosensitizing characteristics due to internal energy transfer and ultimately the long-term instability of the formulation itself, hindering its commercial development.

EP0720853 describes a topically administerable formulation comprising:
(A) Zn-phthalocyanine,
(B) as excipients for the formulation of (A),
  (i) a diethylene glycol monoalkyl ether substantially in the absence of an N-alkylpyrrolidone, an N, N-dialkylbenzamide or dimethyl sulfoxide, or
  (ii) a mixture of a diethylene glycol monoalkyl ether with a lipid; and
(C) a gelling agent.

Simonetti et al. (British J. Dermatology 2011, 164(5), 987-995) describes a topical gel formulation comprising RLP068/Cl (at various concentrations 0.01%, 0.1%, 0.3% and 0.5%), a mixture of alcohols gelled with an appropriate concentration of a carboxymethyl cellulose polymer.

The aim of the present invention is to provide an improved formulation suitable for topical administration, containing a zinc phthalocyanine photosensitizer, preferably with hydrophilic substituents and in particular of a cationic nature. This formulation must be suitable for letting the photosensitizer penetrate into the epidermis, where the skin affections are mostly localized, without however affecting the dermis, thus avoiding reaching the systemic circulation and therefore unwanted absorption. The aim of the present invention is also to provide formulation which is stable over time.

SUMMARY OF THE INVENTION

Subject-matter of the present invention is a composition suitable for topical administration comprising or consisting of:
(a) a Zn-phthalocyanine derivative as a photosensitizing agent;
(b) a diethylene glycol monoalkyl ether as a cutaneous permeation promoter contained in amounts of 3-35% w/w,
(c) a solvent selected from the group consisting of propylene glycol and polyethylene glycol, of various molecular weight;
(d) optionally a cutaneous permeation co-promoter selected from the group consisting of EtOH and iPrOH;
(e) a viscous agent selected from the group consisting of hydroxypropyl cellulose (HPC), hydroxymethylpropylcellulose (HMPC), polyvinyl alcohol (PVA), carboxymethylcellulose (CMC);

wherein said Zn-phthalocyanine derivative (a) is of formula (I)

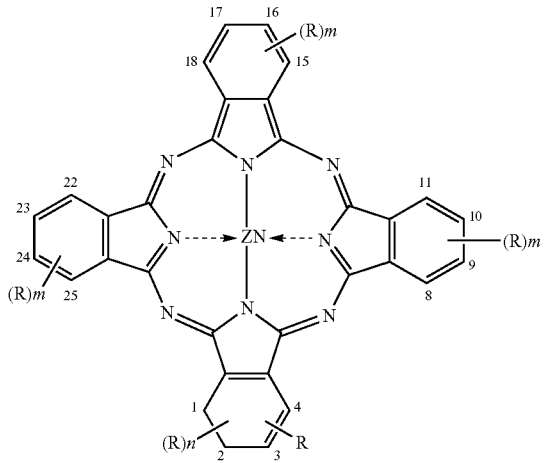

(I)

wherein
R is

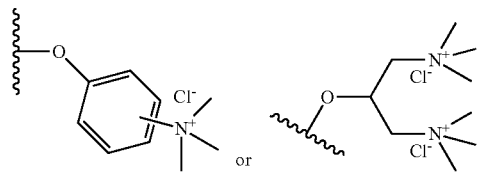

n=0, 1 and m=0, 1, 2 where when n=0 then m=0, 1, when n=1 then m=0, 2.

The subject of the present invention relates to a non-aqueous formulation suitable for topical localized administration and therefore is useful for the localized therapy of skin and mucosal affections.

The formulation of the present invention allows the penetration of the photosensitizer into the epidermis, preferably localized in the superficial layers of the skin, with poor penetration into the dermis thus avoiding reaching the systemic circulation and therefore avoiding a systemic exposure to the photosensitizer or to the products of photo decomposition of the phthalocyanine product following irradiation. It is in fact known that many derivatives with this chemical structure undergo a process of photo decomposition (Photobleaching) following radiation even with visible light which leads to the fragmentation of the macrocyclic ring of the photosensitizer.

The present formulation also has very low toxicity also by virtue of the absence of preservatives, stabilizers and products which, although they are widely used in topical formulations as permeation promoters, also for cosmetic use, have demonstrated in this context an undesired localized toxicity such as Tea Tree Oil (TTO), (±)-α-bisabolol (BIS) and isopropyl myristate (MYR).

The present formulation also has stability over time.

With regards to one aspect, the present invention also relates to a process for preparing the above composition.

DETAILED DESCRIPTION OF THE INVENTION

The formulation according to the present invention is preferably in the form of a non-aqueous transparent gel.

The formulation can in some cases be sterile, by way of a series of known processes suitable for sterilizing the composition, as better detailed below. The fact of being transparent and not corpusculated or not consisting of an emulsion allows an optimal passage of visible light, at the suitable therapeutic wavelength used. The fact of being non-aqueous makes it an environment not subject to contamination and growth by microorganisms and as anticipated the formulation can also be sterilized. Preferably the composition, object of the present invention, has a viscosity comprised between 25 and 190000 cP: in some embodiments the viscosity is 25-65 cP, in other embodiments the viscosity is 50000-190000 cP (where cP stands for centiPoise). This viscosity is determined by using capillary (range 25-65 cP) or rotational (range 50000-190000 cP) viscometers. The formulations with viscosity 25-65 cP are liquid formulations useful for the treatment of those skin affections characterized by deep lesions in which the formulation can creep, formulations with viscosity 50000-190000 cP are semi-solid formulations useful for the treatment of those skin affections characterized by superficial lesions on which the formulation can remain without dripping away.

The composition of the present invention is preferably free of
 other promoters of skin permeation, in particular free of essential oil of Tea Tree (TTO), (±)-α-bisabolol (BIS) and isopropyl myristate (MYR);
 preservatives, in particular free of mixtures of parabens and/or phenoxy ethanol;
 stabilizers, in particular free of alpha-tocopherol acetate (vit E).

TTO, in addition to being a known promoter of skin permeation, also has a significant antimicrobial and antifungal activity and therefore the use thereof in the formulation should have led to a synergistic interaction with the same therapeutic activity of the photosensitizer.

Surprisingly, it has instead been found that the presence of TTO in the composition facilitates the passage of the photosensitizer in the systemic circulation, therefore making the composition less suitable for topical localized application as is the object of the present invention, therefore it is preferable that the composition is free of TTO. An additional reason for the exclusion of TTO is associated with the variable composition of the TTO composing components. Being a natural product there is the possibility that the composition of the product varies and this is in contrast with the need for rigorous characterization in the case of formulations for therapeutic use.

(±)-α-bisabolol (BIS) and isopropyl myristate (MYR) are promoters of skin permeation and in the case of the present composition it has occurred that they produce undesirable effects with respect to the objective of the present invention. In particular, the tested compositions containing MYR were toxic in the in vivo tests causing skin ulcers in experimental animals and therefore the presence of this/these component/s should preferably be avoided.

Alpha-tocopherol (vitamin E) is often included in pharmaceutical compositions for topical application as an antioxidant. Vitamin E is a vitamin necessary for human beings in whom it is introduced through a special diet. Thanks to its powerful antioxidant and lipophilic properties, vitamin E is known for the protection of epidermal cell membranes and lipids from oxidation damage. Numerous studies have shown that vitamin E has the property, by topical administration, of reducing both chronic and acute skin irritations such as erythema and oedema, an effect likely linked to a process of singlet oxygen quenching and/or other reactive radicals of the oxygen, generated endogenously by macrophages in the presence of inflammation processes.

Surprisingly, it has been found that in the presence of vit E in the formulations of the present invention, no effect attributable to a quenching process of any reactive species generated during the photodynamic treatment in vivo has been detected. In fact, the total elimination thereof did not increase chronic and acute skin irritations such as erythema and oedema.

Furthermore, the absence of vitamin E in the formulations of the present invention did not negatively influence the long-term stability data.

Therefore, the presence thereof in the formulation is superfluous and justifies the choice to keep the composition of the formulation as simple as possible.

The photosensitizer (a) in the formulation according to the present invention is preferably a compound of formula (I) wherein:
n=0, m=0 and
R, in position 1 or 2, is

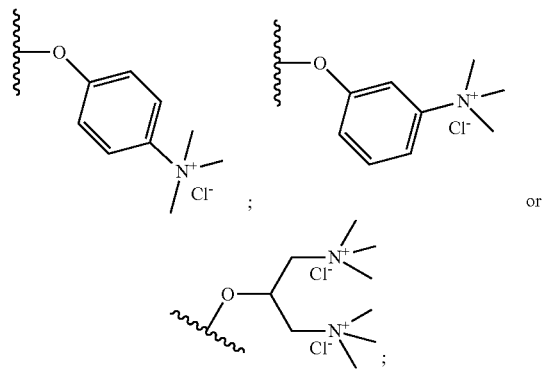

or
n=1, m=0 and
R, in positions 1,4 or 2,3, is

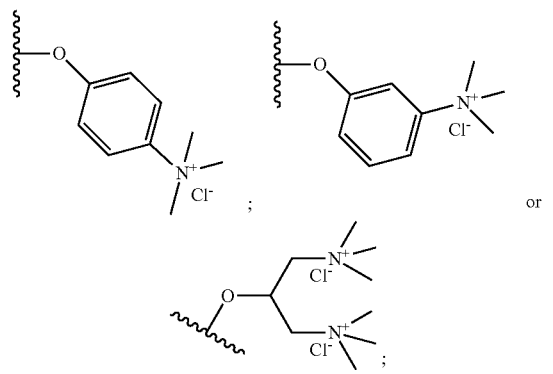

or
n=0, m=1 and
R, in positions 1,8(11),15(18),22(25) or 2,9(10),16(17), 23(24), is

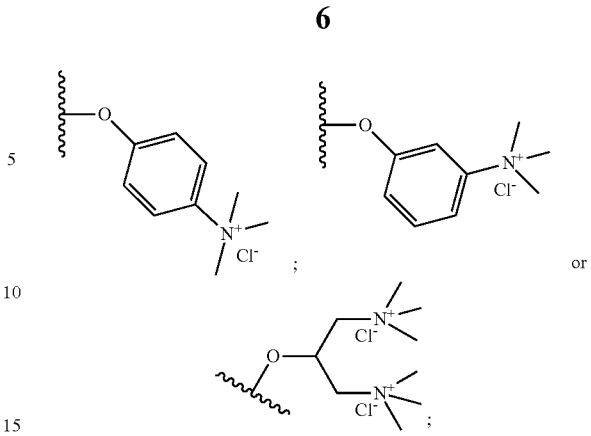

or
n=1, m=2 and
R, in positions 2,3,9,10,16,17,23,24, is

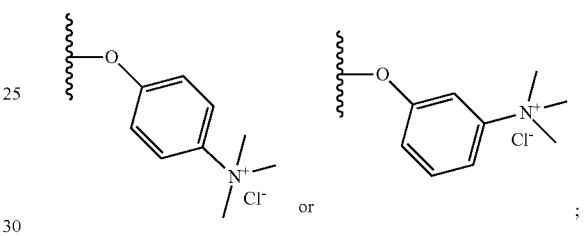

In a particularly preferred way, the photosensitizer (a) in the formulation according to the present invention is 1,8 (11),15(18),22(25)-Tetra[3-(N,N,N-trimethylammonium) phenoxy]zinc phthalocyaninate (II) tetrachloride (hereinafter also identified as RLP068/Cl). In the composition according to the present invention, the compound RLP068/Cl is preferably present in the form of a mixture of positional isomers as described in WO2011/012698, i.e. of the four positional isomers, identified according to the classes of symmetry ($D_{2h}$, $C_{4h}$, $C_s$, $C_{2v}$), and named below, respectively, with the letters of the alphabet (A, B, C, D) the isomer B is present in amounts equal to or less than 1% by weight.

The diethylene glycol monoalkyl ether is usually an alkyl $C_1$-$C_4$ ether of this glycol, for example methyl, ethyl, n-propyl, isopropyl or n-butyl one. A particularly preferred monoalkyl ether is the diethylene glycol ethyl ether. Preferably, therefore, the composition according to the present invention comprises diethylene glycol monoethyl ether [also known as 2-(2-Ethoxyethoxy)ethanol] as permeation promoter (b). 2-(2-Ethoxyethoxy)ethanol or Transcutol® P (trade name) acts as a solvent for the photosensitizer and as an agent to promote the penetration of the photosensitizer into the stratum corneum of the skin, without causing systemic availability.

Transcutol® P has been in use for many years in the pharmaceutical and cosmetic field and is therefore considered a product with adequate safety for clinical use.

Said solvent selected from the group consisting of propylene glycol and polyethylene glycol, at various molecular weight, has a molecular weight of 200-600 g/mol. Preferably the composition according to the present invention comprises propylene glycol (PG) as a co-solvent (c). Propylene glycol is the main component of the composition in one of its preferred embodiments, as well as the main solvent for the photosensitizer and topical agent for improving the penetration of visible light into the skin. It is known that the application of agents such as propylene glycol or glycerol reduces the difference of the refractive indices of the skin layers and greatly minimizes the random dispersion of light, so as to improve its penetration into the skin layers at visible wavelengths for a controlled period of time. This property, also known as "optical compensation", leads to a better activation of the composition according to the present invention within the lesion by the therapeutic light used for the activation of the photosensitizers mentioned in the present invention.

Preferably the composition according to the present invention comprises Ethanol as a permeation co-promoter (d). It is widely used in topical gels or in transdermal products even at much higher concentrations than that preferably used in the present composition. The presence of Ethanol at the concentrations indicated below is free of toxic and/or irritating action.

Preferably the composition according to the present invention comprises hydroxypropyl-cellulose (HPC) as a viscous agent (e). HPC is preferably used as a thickener to give the composition of the present invention the desired rheological property. The viscosity of the composition according to the present invention has been optimized to obtain a satisfactory topical application and to reduce the problems associated with the loss from the treatment site before irradiation. Furthermore, the chosen composition of the formulation ensures an optical transparency to the therapeutic light and the lack of dispersion of the same.

Preferably in the composition according to the invention the photosensitizer (a) is contained in amounts of 0.05-0.5% w/w, more preferably 0.1-0.3% w/w.

In the composition according to the invention, the diethylene glycol monoalkyl ether (b) is contained in amounts of 3-35% w/w, more preferably 5-10% w/w.

Preferably in the composition according to the invention the solvent (c) is contained in sufficient amounts to complete the composition at 100% w/w. Since the product/s is/are hygroscopic, the amount of photosensitizer used can be varied on the basis of the title of each batch, consequently varying the amount of propylene glycol and leaving the final concentrations of the other components in the composition unchanged.

Preferably in the composition according to the invention, the co-promoter (d) is contained in amounts of 0-15% w/w, more preferably 0-10% w/w.

Preferably in the composition according to the invention the viscous agent (e) is contained in amounts of 0.05-3% w/w, more preferably 0.1-2% w/w. For formulations the viscosity of which is 25-65 cP it is preferable to use a viscous agent with a low degree of viscosity (such as Klucel JF) and in amounts of 0.1-0.2% w/w. For formulations the viscosity of which is 50000-190000 cP it is preferable to use a viscous agent with a high degree of viscosity (such as for example Klucel HF) and in amounts of 1-2% w/w.

Preferably the composition according to the invention is consisting of:

| (a) | RLP068/Cl | 0.1-0.3% w/w |
| (b) | diethylene glycol monoethyl ether | 5.0-10.0% w/w |
| (c) | propylene glycol | q.s to 100% w/w |
| (d) | EtOH | 0-10.0% w/w |
| (e) | hydroxypropyl cellulose | 0.1-1.5% w/w |

A preferred embodiment of the composition (PLUS formulation) according to the invention is consisting of:

| (a) | RLP068/Cl | 0.3% w/w |
| (b) | diethylene glycol monoethyl ether | 5.0% w/w |
| (c) | propylene glycol | q.s to 100% w/w |
| (e) | hydroxypropyl cellulose (Klucel JF) | 0.1% w/w |

Another preferred embodiment of the composition (GEL formulation) according to the invention is consisting of:

| (a) | RLP068/Cl | 0.3% w/w |
| (b) | diethylene glycol monoethyl ether | 10.0% w/w |
| (c) | propylene glycol | q.s to 100% w/w |
| (d) | EtOH | 10.0% w/w |
| (e) | hydroxypropyl cellulose (Klucel HF) | 1.5% w/w |

Another preferred embodiment of the composition according to the invention is consisting of:

| (a) | RLP068/Cl | 0.1% w/w |
| (b) | diethylene glycol monoethyl ether | 10.0% w/w |
| (c) | propylene glycol | q.s to 100% w/w |
| (d) | EtOH | 10.0% w/w |
| (e) | hydroxypropyl cellulose (Klucel HF) | 1.5% w/w |

% w/w are calculated on the total weight of the composition.

The composition subject-matter of the present invention is useful for the photodynamic treatment (PDT) of skin or mucosal affections.

The composition subject-matter of the present invention is used in combination with activation with a red light and preferably in a wavelength range between 600-700 nm. The irradiation of the phthalocyanine photosensitizer with the light of the specified wavelength generates singlet oxygen and radicals mainly of transient oxygenated species (ROS, Reactive Oxygen Species) that have an average life equal and limited to a few nanoseconds since, given the particular reactivity, are readily inactivated by cellular components. Since the photosensitizers mentioned in the present invention are mainly linked to membrane and/or wall components, cellular damage occurs in a few (a few tens) nm, the distance allowed by the average life time of the ROS species. It is for example widely recognized that ROS have a cytotoxic action on Gram (+) pathogens such as the bacterium *Staphylococcus* spp, *Streptococcus* spp, Gram (−) pathogens like *Escherichia coli*, *Acinetobacter baumanni*, *Klebsiella* spp, *Moraxella* spp, yeasts like *Candida* spp and protozoa like *Leishmania* spp, Acantamoeba spp and many others. The mechanism of action for inactivation takes place mainly at the level of membrane lipids of microorganisms similarly to what is reported in the literature with regards to the inactivation of microorganisms by neutrophils through the physiological process.

The formulation according to the present invention is therefore useful, in combination with an irradiation with a red light, for the topical localized treatment of skin infections of microbial origin from Gram (+), Gram (−) pathogens, yeasts, fungi and protozoa.

The presence of low, therefore non-lethal, concentrations of the photosensitizer on the host cells, for example in the perilesional areas, can have a stimulating effect on the repair and scarring processes that occurs concomitantly with that of bacterial inactivation, favouring a micro environment for the healing of lesions (Nesi-Reis V. et al. Photodiagnosis Photodyn Ther. 2018 March; 21:294-305; Wounds International, 2016; Reinhard A. et al. Expert Rev Clin Immunol. 2015 May; 11(5):637-57).

The compositions subject-matter of the present invention are applied topically on superficial wounds or superficial skin ulcers and a systemic absorption has not been found. The composition subject-matter of the present invention in the context of PDT is an effective adjuvant also for the local treatment of superficial skin wounds and ulcers since, after photo activation, it modulates with physical action, the microenvironment of the lesions to facilitate the healing thereof.

The further advantages of use of the composition subject-matter of the present invention are reported below:

- the treatment can be modulated over time (⅔ vv per week for a few weeks). It can also be started and discontinued simply by irradiating or stopping irradiation;
- the treatment does not require any effort from the patient; it acts only in the irradiation area, therefore it is a specific treatment without side effects at a distance from the treatment site as is the case for antimicrobial drugs;
- the cost-benefit ratio as a whole is positive;
- the therapeutic treatment of the patient is not a problem since the procedure can be carried out by health professionals during normal medical visits and check-ups;
- at the discretion of the physician, systemic administration of antibiotics may be reduced or eliminated;
- the treatment may however include the simultaneous use of antibiotics systemically;
- in the case of infected lesions, the identification of the microorganisms that caused the infection is not required since the treatment guarantees the microbial inactivation of Gram+ and Gram− species, fungi and protozoa, therefore a broad spectrum inactivation and is not influenced from antibiotic resistance having confirmed that PDT treatment is equally effective on both wild type microorganisms and on those that have developed resistance to antibiotics.

Furthermore, the proposed PDT treatment does not generate itself resistances since it is an inactivation based on a chemical physical process of the multitarget type, and not generated by an interference with a metabolic process as for antibiotics.

The composition subject-matter of the present invention can therefore contribute to facilitate the healing of superficial skin wounds, improving the patient's quality of life and maintaining a positive profile with regards to safety and tolerability aspects. It constitutes a valid approach for the treatment of lesions and the acceleration of the healing of superficial wounds of various nature.

Preferably, the process for the preparation of the composition according to the present invention comprises the methods described below.

In the case of semi-solid sterile formulations with viscosities equal to 50000-190000 cP the components (b)-(d) are sterilized by filtration on 0.2 μm membranes together with photosensitizer (a), after dissolution in the aforesaid components (b)-(d). The viscous agent (e), on the other hand, is autoclaved (at 121° C. for 15 minutes) after mixing with the co-solvent (c).

The two sterile solutions thus obtained are combined under aseptic conditions in a sterile insulator. The composition of the invention is preferably packaged, still under aseptic conditions, in disposable amber glass sterile, pyrogen-free bottles of the type I Schott VADIN2R, sealed by a closure system of butyl chlorine coated with Flurotec Plus and a completely sealing aluminium ring nut previously sterilized by heat.

In the case of sterile formulations with a viscosity equal to 25-65 cP all the components and the photosensitizer, after complete dissolution, are sterilized by filtration on 0.2 μm membranes.

Preferably, the sterile formulation is inserted in polyethylene strips consisting of 5 single-dose 2 mL vials previously sterilized with gamma radiation.

In the case of non-sterile semi-solid formulations with varying degrees of viscosity, all the components and the photosensitizer are mixed until complete dissolution, guaranteeing the maintenance of a low microbial load to the final formulation.

Preferably, the non-sterile formulation is inserted in polyethylene strips consisting of 5 single-dose 3 mL vials previously sterilized with gamma radiations.

For the purposes of the present invention the terms "composition" and "formulation" are intended as synonyms.

The present invention can be better understood in the light of the following embodiment examples.

EXPERIMENTAL PART

1. Materials 1,8(11),15(18),22(25)-Tetra[3-(N,N,N-trimethylammonium)phenoxy]zinc phthalocyaninate (II) tetrachloride (Zn-Ftalocianina, RLP068, Molteni Therapeutics S.r.l., Italy)

Diethylene glycol monoethyl ether (Transcutol® P, Gattefossè, France)

Hydroxypropyl cellulose (Klucel HF Pharm, Hercules, Holland)

Essential oil of Tea Tree Oil (TTO, Main Camp® Pharmaceutical Grade Tea tree oil, Variati & Co., Italy)

Isopropyl myristate (MYR, Merck, Schuchardt, Germany)

(±)-α-bisabolol (BIS, BASF, Germany)

Propylene glycol (PG, Acef S.p.A, Italy)

Polyethylene glycol 200 (PEG 200, Merck, Schuchardt, Germany)

Sodium dodecyl sulphate (SDS, Sigma-Aldrich S.r.l., Milan, Italy).

All the salts and solvents used were of analytical or HPLC grade.

2. Methods 2.1. In Vitro Transdermal Permeation Studies 2.1.1. Skin Models

Animal Skin

Hairless rat skin was used as a model of animal skin for "in vitro" skin permeation studies due to its easy availability and ease of use and given the similarity in thickness and structure with the human skin. On both the dorsal and abdominal surfaces, it does not adhere to the viscera and can thus be easily removed maintaining a uniform thickness, without resorting to microtomy. Female 5-week hairless rats were used (OFA-hr/hr, Charles River Italia SpA). Immediately after being sacrificed by cervical dislocation of the spine, the intact skin was carefully cut and the dermis was carefully freed from any adhesion of subcutaneous tissue and blood vessels. Portions each of about 3 cm side were cut and used for "in vitro" permeation and distribution experiments.

Human Skin

Human skin explanted from Caucasian female patients who underwent abdominal plastic surgery was used.

The term "viable human skin" indicates fresh skin used immediately after surgery; the term "nonviable human skin" indicates skin frozen after surgery and used afterwards.

Nonviable human skin has been used in this description; immediately after removal, the subcutaneous fat was removed and the skin preserved until use at −20° C. in waterproof aluminium sheets. The skin samples were frozen for no longer than 6 months; numerous studies have in fact demonstrated that there are no structural changes that affect the permeability of the drug when human skin is frozen for such a period of time (Harrison and Barry, 1984; Bronaugh et al., 1986).

2.2. In Vitro Release Studies

Figure 1:
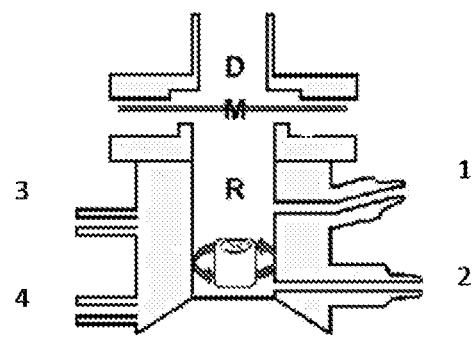
FIG. 1—Vertical diffusion cell of the Gummer type (1,2: inlet and outlet of the receptor phase; 3,4: inlet and outlet of the thermostating water)

The "in vitro" release studies were performed using the vertical diffusion cell described by Gummer et al. (1987, FIG. 1). This cell consists of a donor compartment (D), a layer of skin (M) and a receptor compartment having a volume of 5.0 ml and a diffusion area of 3.14 cm$^2$ The receptor solution was stirred with a magnetic stirrer at a constant speed of 600 rpm and the temperature of the receptor compartment was controlled by circulating water thermostated at 37° C. in the double wall of the cell.

In the present study, phosphate buffer 66.7 mM, pH=7.4, isotonized with sodium chloride (0.44 g/100 ml), and containing sodium azide (0.003%) as a preservative was used as the receptor phase.

The formulations under study were used as the donor phase.

In all cases, at suitable time intervals, approximately 5 ml of solution were withdrawn from the receptor compartment, replacing them with an equal volume of fresh buffer. The amount of drug present in the samples was determined by HPLC. The experiments lasted 5 hours and were carried out in series of at least four.

2.3. Techniques for Separating the Skin Layers

To evaluate the amount of drug distributed within the various skin layers after the permeation tests, two different techniques for separating the skin layers were used: mechanical separation and separation by cryomicrotome.

2.3.1. Mechanical Separation

This technique consisted in the separation of the epidermis from the dermis through light "scraping" of the skin carried out with the edge of a metal spatula. This mechanical removal made it possible to effectively separate the epidermis from the dermis, whose consistency and visual appearance clearly differed from the epidermis.

Each layer, suitably cut into small pieces and weighed, was put in contact with 2 ml of a 2% solution of sodium dodecyl sulphate (SDS), subjected to stirring for 24 hours at room temperature in order to obtain a partial digestion. Subsequently, to complete digestion, 3 ml of a MeOH/CHCl$_3$ (2:1) mixture were added, continuing the stirring for another hour. After centrifugation at 5000 rpm for 15 minutes the subnatant was withdrawn. Given the presumed small amount of drug distributed inside the skin, the subnatant solution divided into aliquots was dried, the residue was subsequently taken up with MeOH and the amount of extracted phthalocyanine was determined by HPLC.

2.3.2. Separation by Cryomicrotome

This technique has allowed us to section the part of the skin coming from the in vitro permeation tests into much more detail.

Figure 2:
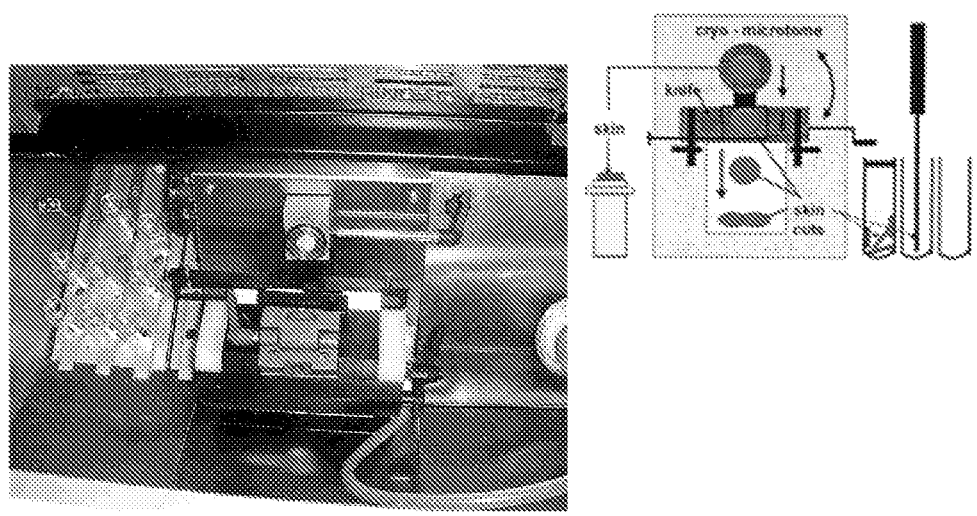
FIG. 2—Photograph of the cryomicrotome mod. Mev Slee Technik GMBH and skin sectioning scheme.

The skin sectioning procedure was performed at −25° C. with a cryomicrotome (Cryostat mod. Mev Slee Technik GMBH, Mainz, Germany). FIG. 2 shows the photograph of the front part of the cryomicrotome and a scheme of the sectioning phases.

The skin was stretched and bonded on the appropriate support with the part of the epidermis facing upwards and was flattened as much as possible by placing a 1 kg weight thereon for a standardized time (one minute). The support was then introduced into the cryomicrotome where, for a few seconds, a slight pressure parallel to the support was exerted on the skin by means of a plastic disk. This operation proved to be very important for obtaining complete sections of the skin in the first layers of the epidermis, so as to follow the "path" of the phthalocyanine already from the most superficial layers. After freezing, the skin was sectioned into 25 μm thick samples and the various skin sections harvested in previously calibrated vials, putting all fragments of incomplete slices in the first one, the first complete 25 μm slice in the second one and so on according to a standardized scheme shown in Table 1.

Taking into account that presumably the amount of active ingredient in the sections decreases with the increase of skin depth (therefore of the number of sections), in order to obtain an amount of phthalocyanine higher than the sensitivity limit of the analytical method, the sections corresponding to the deepest part of the skin were harvested in the same vial.

Finally, the residue of the skin, from which it was no longer possible to obtain a complete section, was placed in the last vial.

TABLE 1

Skin harvest scheme after subdivision

|  | Number of slices | Total μm |
| --- | --- | --- |
| Vial 1 | Incomplete slices | Unknown |
| Vial 2 | 1 | 25 |
| Vial 3 | 1 | 25 |
| Vial 4 | 2 × 25 | 50 |
| Vial 5 | 4 × 25 | 100 |
| Vial 6 | 4 × 25 | 100 |
| Vial 7 | 4 × 25 | 100 |
| Vial 8 | 4 × 25 | 100 |
| Vial 9 | 4 × 25 | 100 |
| Vial 10 | 4 × 25 | 100 |
| Vial 11 | 4 × 25 | 100 |
| Vial 12 | 4 × 25 | 100 |
| Vial 13 | 4 × 25 | 100 |
| Vial 14 | Residue | Unknown |

Each vial was weighed in order to know the weight of skin present in each of them. The thickness of the incomplete portions and the residue was calculated on the basis of their weight, referring to layers of skin of known thickness and weight. The formula used was the following:

$$\text{Incomplete section thickness} = \frac{\sum \text{Section thickness}}{\sum \text{section weight}} \times \text{incomplete section weight}$$

Subsequently, each section was digested, so as to extract the drug, with the method previously described for mechanical separation, adapting suitable amounts of solvents in relation to the amount of skin to be treated.

For this purpose, 1 ml of 2% SDS was added to each vial for 24 hours, and then 1.5 ml of MeOH/CHCl$_3$ (2:1) mixture for 1 hour. Finally, an aliquot of subnatant was dried under vacuum to take up the residue with MeOH.

Finally, the amount of phthalocyanine in the various skin sections was determined, as in the previous method, by HPLC.

3. Analytical Methods
3.1. Quantitative Determination of RLP068

The quantitative analysis of the photosensitizer present both in the receptor phase of the "in vitro" permeation studies and within each skin layer, after separation and extraction treatment, was carried out using the HPLC method.

Shimadzu LC-10AS equipment was used with SPD-10AV UV detector, equipped with SIL-10AD VP autosampler and appropriate integration software.

The injection valve was a Rheodyne with a capacity of 20

The reverse phase column was a Bondclone (Phenomenex) 30 cm long and with 3.9 mm internal diameter, packed with a 10 μm C$_{18}$ phase.

The conditions of analysis, mobile phase, flow, retention time and detection wavelength of the photosensitizer are summarized in Table 2.

TABLE 2

HPLC analysis conditions.

| Drug | Mobile phase (ratio) | Flow (ml/min.) | Retention time (min.) | Wavelength (nm) |
| --- | --- | --- | --- | --- |
| RLP068 | MeOH:CH$_3$CN:Slz.A* (55:20:25) | 1 | 11.40 | 361 |

*Slz.A: 1.0312 g of sodium hexasulfonate in 100 ml of H$_2$O brought to pH = 3 with glacial AcOH For the "in vitro" transdermal permeation tests, the quantitative analysis of the photosensitizer in the samples was performed by comparison with external calibration curve obtained by diluting a stock solution in methanol with isotonic phosphate buffer at pH=7.4 containing sodium azide (0.003% w/v).

The quantitative analysis of the photosensitizer extracted from the skin after the permeation tests was carried out by comparison with calibration curves obtained by adding known aliquots of photosensitizer in methanolic solution to blank skin samples (not previously treated with phthalocyanine) and treating as previously described.

The selectivity of the test specimen was confirmed by individually analysing blank samples of both the skin layers and the receptor phase of the diffusion cells. With the described analysis method, the absorption peaks related to RLP068 both after extraction from the skin layers and in the receptor phase were well resolved.

The calibration curves were linear in the range of 0.78-15.45 μM for the samples extracted from the skin and 0.65-4.00 μM for the samples of the receptor phase.

Linear regression analysis showed correlation coefficients greater than 0.998 in all cases.

3.2. Formulations Under Study

Semi-solid formulations based on RLP068 were prepared using Transcutol® P as a solvent and containing Klucel HF® as a viscous agent and capable of giving rise to transparent gels. The formulations differ from each other not only in the concentration of the photosensitizing agent, comprised between 0.066% and 0.264% (0.5-2 mM), but also in the type of promoter and the concentration thereof inside the vehicle. In some cases a part of Transcutol® P was replaced with a cosolvent, EtOH or PG, to verify a possible synergy action between cosolvent and permeation promoter in favouring the accumulation of phthalocyanine in the skin layers. All prepared formulations are shown in Table 3.

The vehicle Gel 1 containing RLP068 1 mM (0.132% w/w), Transcutol® P and Klucel® HF (analogous to the formulation described in EP0720853A1 example 2) was prepared as a reference formulation. This formulation was therefore modified with the addition of PG (Gel 2) in order to see the effect of the cosolvent on the accumulation of photosensitizer in the skin layers. For the same reason the vehicle Gel 3 containing also EtOH in addition to Transcutol® P and PG was prepared.

Other vehicles were then prepared using three different concentrations of RLP068, in order to evaluate the effect of the concentration of the active ingredient on the amount accumulated in the skin layers, in the absence (Gel 5, Gel 4, Gel 6) and in the presence of TTO (Gel 8, Gel 7, GEL 9) as a promoter of skin penetration. The formulation containing the highest concentration of photosensitizer was prepared at two different concentrations of TTO, 20 and 0.25% respectively for vehicles Gel 9 and Gel 10, in order to study the influence of the concentration of the promoter RLP068 on the skin penetration.

Since TTO, in addition to being a promoter of skin permeation, also has a good antimicrobial and antifungal activity, its use in the formulation could lead to an interaction with the therapeutic activity of the photosensitizer. For this reason, two new promoters of skin permeation have been tested: (±)-α-bisabolol (BIS) and isopropyl myristate (MYR).

(±)-α-bisabolol was used at two different concentrations, 20 and 6% for the formulations Gel 11 and Gel 12 respectively, containing 20% ethanol as a cosolvent. The same formulations, prepared using isopropyl myristate as a promoter at 20% and 6% concentrations, have been indicated respectively with the abbreviations Gel 14 and Gel 15.

Two vehicles were then prepared containing the promoter in only Transcutol® P and Klucel® HF, one containing 20% of (±)-α-bisabolol (vehicle Gel 13), the other one containing 6% of isopropyl myristate (vehicle Gel 16).

TABLE 3

W/w percentage composition of semi-solid vehicles based on RLP068.

| Formulation RLP068 | RLP068 | TTO | MYR | BIS | EtOH | PG | Klucel ® HF | Transcutol ® P |
|---|---|---|---|---|---|---|---|---|
| Gel 1 | 0.132 | — | — | — | — | — | 1.5 | 98.368 |
| Gel 2 | 0.132 | — | — | — | — | 49 | 1.5 | 49.368 |
| Gel 3 | 0.132 | — | — | — | 15 | 49 | 1.5 | 34.368 |
| Gel 4 | 0.132 | — | — | — | 20 | — | 1.5 | 78.368 |
| Gel 5 | 0.066 | — | — | — | 20 | — | 1.5 | 78.434 |
| Gel 6 | 0.264 | — | — | — | 20 | — | 1.5 | 78.236 |
| Gel 7 | 0.132 | 20 | — | — | 20 | — | 1.5 | 58.368 |
| Gel 8 | 0.066 | 20 | — | — | 20 | — | 1.5 | 58.434 |
| Gel 9 | 0.264 | 20 | — | — | 20 | — | 1.5 | 58.236 |
| Gel 10 | 0.264 | 0.25 | — | — | 20 | — | 1.5 | 77.986 |
| Gel 11 | 0.132 | — | — | 20 | 20 | — | 1.5 | 58.368 |
| Gel 12 | 0.132 | — | — | 6 | 20 | — | 1.5 | 72.368 |
| Gel 13 | 0.132 | — | — | 20 | — | — | 1.5 | 78.368 |
| Gel 14 | 0.132 | — | 20 | — | 20 | — | 1.5 | 58.368 |
| Gel 15 | 0.132 | — | 6 | — | 20 | — | 1.5 | 72.368 |
| Gel 16 | 0.132 | — | 6 | — | — | — | 1.5 | 92.368 |

4. Results
4.1. Hairless Rat Skin
4.1.1. Transdermal Permeation

All the semi-solid vehicles prepared (Table 3) were subjected to transdermal permeation tests through hairless rat skin using vertical diffusion cells of the Gummer type.

Figure 3:
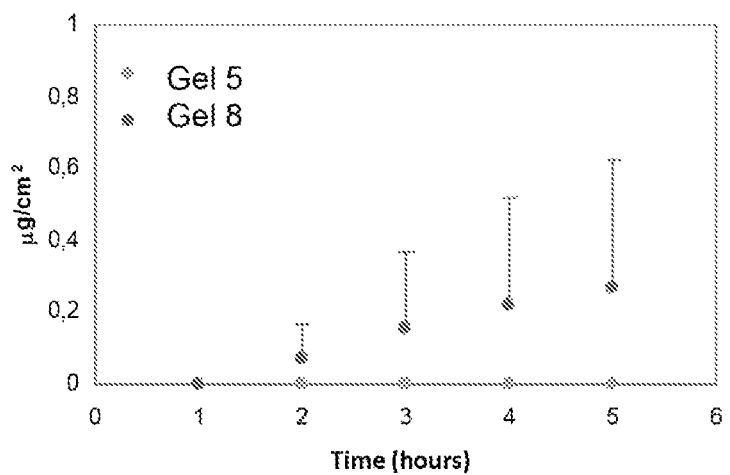
FIG. 3—Permeation profile of RLP068 through hairless rat skin
Figure 3:
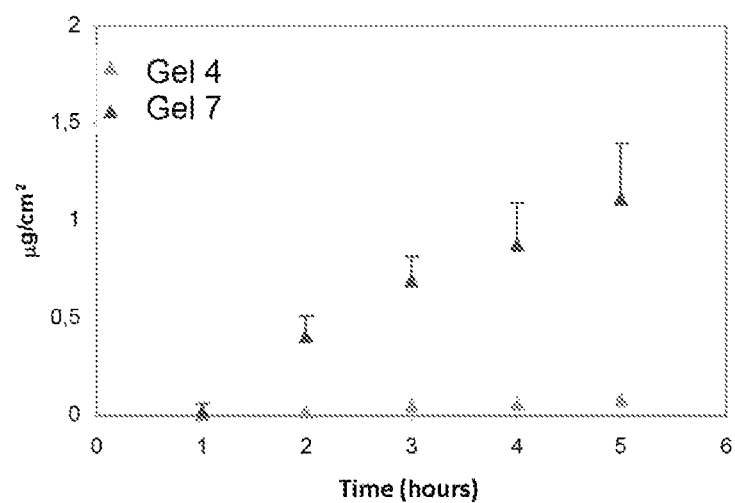
Figure 3:
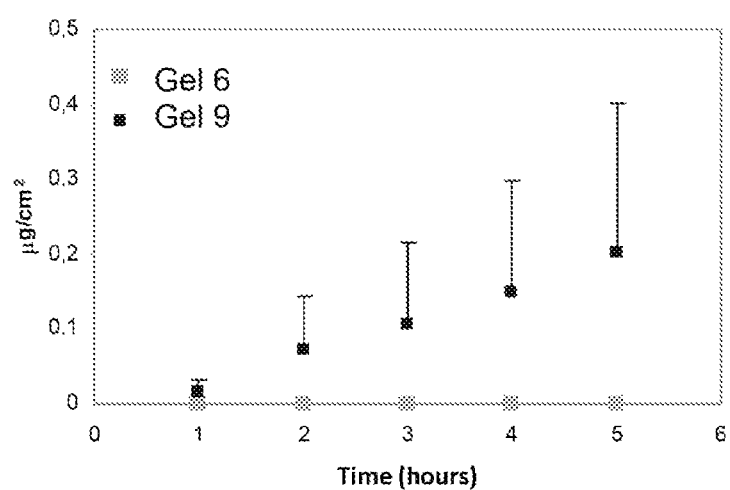
Figure 4:
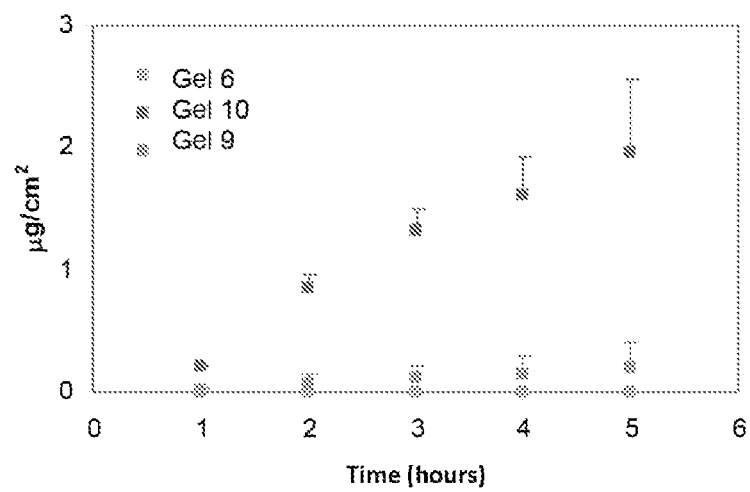
FIG. 4—Permeation profile of RLP068 through hairless rat skin

From the results of the permeation tests through the rat skin, reported in the FIGS. 3 and 4, it should be noted that the formulations Gel 7, Gel 8, Gel 9 and Gel 10 caused a passage of RLP068 in the receptor phase. For all formulations the transdermal permeation is attributable to the presence of TTO, in fact there was an increase in the passage in the receptor phase in the presence of TTO compared to the control without promoter. Also, by decreasing the TTO concentration in the vehicle from 20% (Gel 9) to 0.25% (Gel 10) there was an increase in the passage of RLP068 in the receptor phase.

All the other formulations did not allow the permeation of RLP068: in fact, no appreciable amounts of product were detected in the receptor compartment; the limit of determination (0.65 µM) of the analytical method allowed us to exclude the presence of RLP068 in the receptor compartment.

4.1.2. Skin Distribution
Mechanical Separation of the Skin Layers

The results of the distribution tests of RLP068 in the skin, obtained following mechanical separation, are summarized in numerical form in Table 4.

TABLE 4

Accumulation of RLP068 in the hairless rat skin determined after mechanical separation of the skin layers.

| Vehicle RLP068 | Epidermis µg/g ± SE | Dermis µg/g ± SE |
|---|---|---|
| Gel 1 | 25.51 ± 5.26 | 2.29 ± 0.39 |
| Gel 2 | 53.26 ± 15.07 | 0.49 ± 0.18 |
| Gel 3 | 45.41 ± 17.55 | 2.96 ± 0.87 |
| Gel 4 | 589.89 ± 328.64 | 10.06 ± 2.02 |
| Gel 5 | 448.49 ± 99.90 | 1.53 ± 0.21 |
| Gel 6 | 936.31 ± 362.24 | 7.12 ± 0.04 |
| Gel 7 | 4048.23 ± 1145.84 | 34.51 ± 5.04 |
| Gel 8 | 303.76 ± 88.20 | 7.43 ± 4.30 |
| Gel 9 | 12204.04 ± 3974.57 | 52.10 ± 6.76 |
| Gel 10 | 110.89 ± 54.65 | 3.00 ± 0.50 |
| Gel 11 | 1109.00 ± 144.67 | 22.15 ± 7.59 |

TABLE 4-continued

Accumulation of RLP068 in the hairless rat skin determined after mechanical separation of the skin layers.

| Vehicle RLP068 | Epidermis µg/g ± SE | Dermis µg/g ± SE |
|---|---|---|
| Gel 12 | 381.51 ± 50.39 | 2.97 ± 0.34 |
| Gel 13 | 503.91 ± 119.62 | 2.90 ± 1.32 |
| Gel 14 | 1038.74 ± 214.99 | 10.98 ± 2.68 |
| Gel 15 | 287.22 ± 69.18 | 3.30 ± 0.83 |
| Gel 16 | 184.05 ± 5.03 | 13.73 ± 7.99 |

In all cases the amount of photosensitizer accumulated in the skin layers (epidermis and dermis) is reported in µg/g of skin. The data obtained are expressed as a mean of at least three determinations±standard error (SE).

Figure 5:
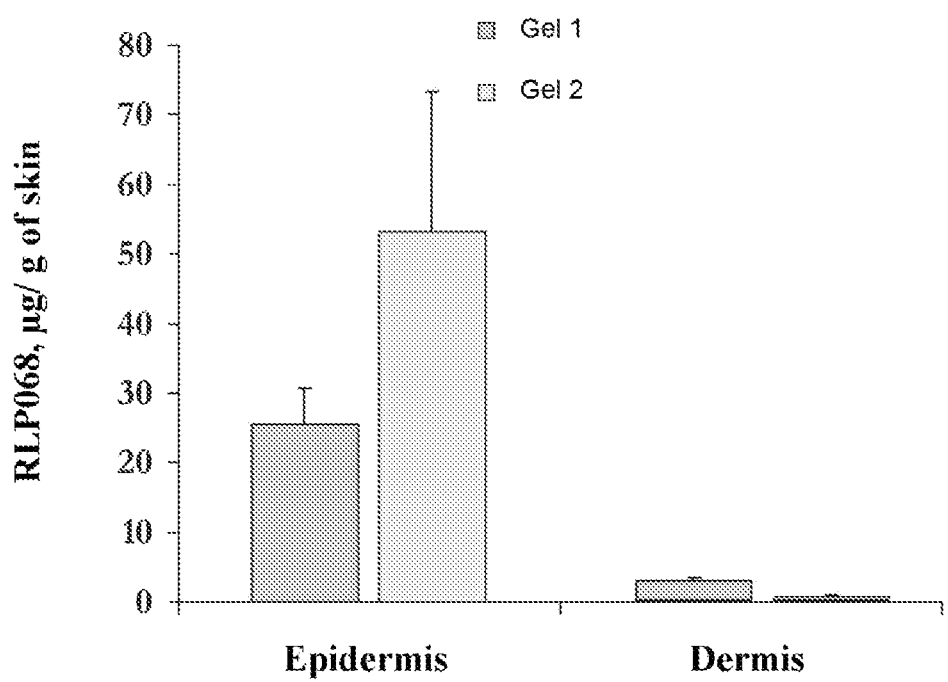
FIG. 5-13—Distribution of RLP068 in the hairless rat skin by using the mechanical separation method FIG. 14—Distribution of RLP068 in the human skin by using the mechanical separation method FIG. 15—Distribution of RLP068 in the human skin by using the separation method by cryomicrotome FIG. 16—Schematic representation of the equipment used for the evaluation of the mucoadhesive properties of the gels FIG. 17—Adhesion work of the formulations under study FIG. 18—Calibration curve obtained for the RLP164 molecule FIG. 19—Calibration curve obtained for the RLP068 molecule FIG. 20—Distribution of RLP068 in the buccal mucosa after application of the formulations for 5 hours. (Mean±s.e., n=3)

When RLP068 is formulated in the vehicle Gel 2, containing Transcutol®P and PG in equal parts (about 49% w/w), there is an accumulation in the epidermis twice that of the vehicle of reference Gel 1, based on only Transcutol®P (FIG. 5). To explain this effect reference can be made to the data in the literature, according to which PG interacts with the polar regions of the skin lipids favouring the passage of Transcutol® P in the skin, which creates a skin deposit of the photosensitizer (Mura et al., Eur. J. Pharm. Sci, 2000, 9, 365-372).

Figure 6:
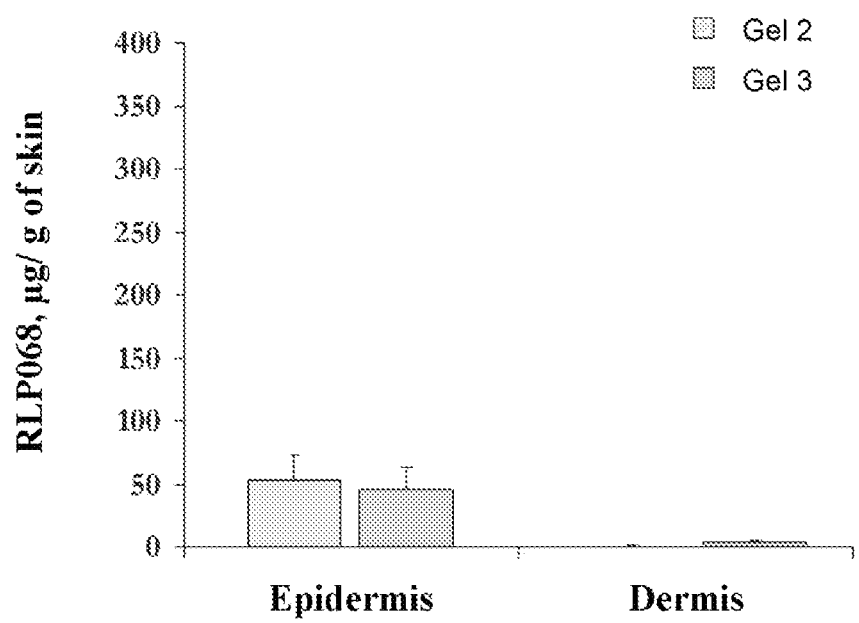

The addition of 15% of EtOH to the formulation (formulation Gel 3) did not lead to an improvement in the accumulation values of RLP068 in the epidermis, the amount of photosensitizer accumulated in the dermis instead increased by about 6 times when compared with the vehicle Gel 2 (FIG. 6). The presence of the cosolvent has therefore ensured that the derivative RLP068 penetrated more deeply into the skin, while leaving the amount accumulated in the epidermis unaltered, therefore not bringing any useful improvement for our purposes. The choice of EtOH was based on the fact that it has both a property as a skin permeation promoter and a documented synergy action with some other promoters. In fact, it is reported in the literature that EtOH penetrates the skin, altering its barrier properties thanks to its action on the lipid component (*Mutalik and Udupa, Pharmazie*, 2003, 58, 891-895). EtOH can also modify the thermodynamic activity of the vehicle: the rapid permeation of a good solvent from the donor phase can leave the photosensitizer in a thermodynamically more active state than when the solvent is present, up to supersaturation point. It has been mostly hypothesized, although this concept is the subject of many controversies and remains to be proven, that the solvent, permeating through the skin, can drag the product therewith (Williams and Barry, *Adv. Drug. Deliv. Rew.*, 2004, 56, 603-618).

Figure 7:
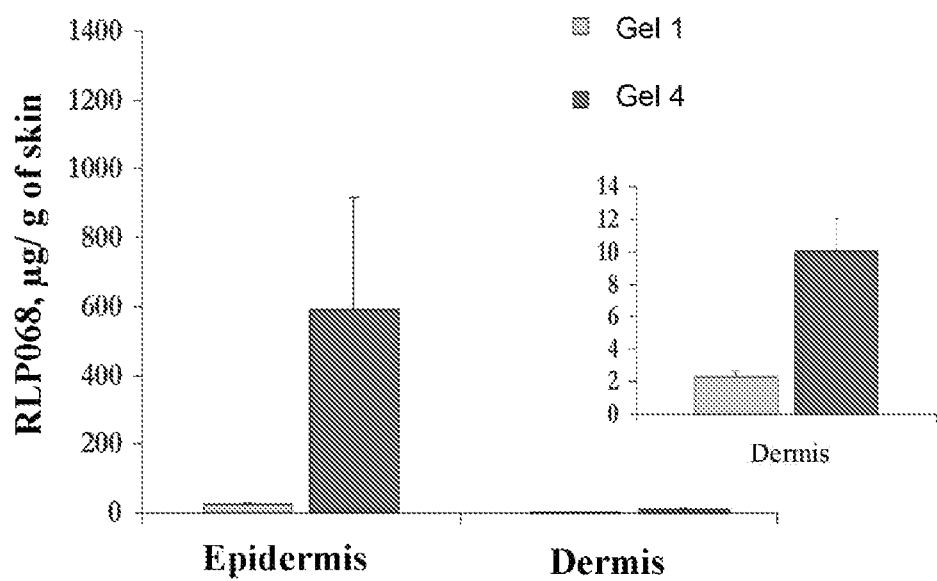
Figure 8:
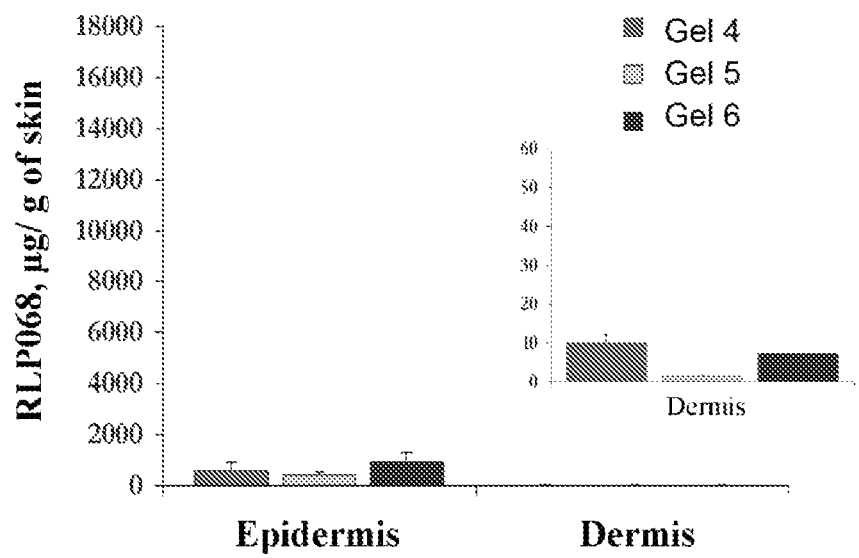
Figure 9:
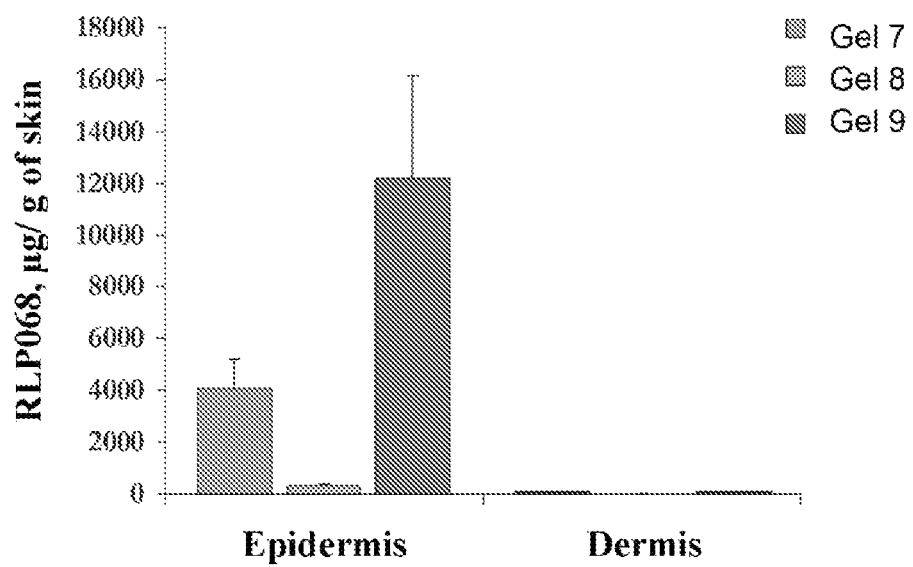

The action of EtOH on the accumulation of photosensitizer in the skin has also been studied both for formulations containing only Transcutol®P and for formulations containing also TTO. These vehicles were prepared using three different concentrations of RLP068, in order to evaluate the effect of the concentration of the photosensitizer on its accumulation in the skin layers, in the absence and in the presence of TTO as a skin permeation promoter. The vehicles Gel 5, Gel 4, Gel 6 were therefore prepared without TTO and containing RLP068 at concentration 0.5, 1 and 2 mM, respectively. The corresponding vehicles containing 20% of TTO were instead indicated with the initials Gel 7, Gel 8, Gel 9. The results of the distribution tests are shown graphically in FIGS. 7-9.

The vehicle Gel 4 containing RLP068 1 mM and 20% of EtOH without TTO, leads to an accumulation in the epidermis about 23 times higher than that obtained with the vehicle Gel 1 based on Transcutol®P only, confirming that EtOH increases the penetration of the photosensitizer into the skin.

In the absence of TTO there are no significant differences between the formulations at different concentration of phthalocyanine both with regards to the accumulation in the epidermis and in the dermis. In fact, 448.49±99.90 µg/g, 589.89±328.64 µg/g, 936.31±362.24 µg/g of RLP068 were found in the epidermis for the formulations Gel 5, Gel 4, Gel 6, respectively.

The presence of 20% of TTO in the vehicle, in addition to increasing the amount of photosensitizer accumulated in the epidermis compared to the control without TTO, enhances the effect of the concentration of RLP068 on the accumulation in the skin layers.

For the formulations Gel 7 and Gel 9, an amount of RLP068 of about 6.86 and 13.03 times higher than that obtained respectively with vehicles Gel 4 and Gel 6, not containing TTO, accumulated in the epidermis. The formulations Gel 5 and Gel 8, however, did not report statistically significant differences in the amounts of RLP068 accumulated in both the epidermis and the dermis.

Furthermore, when the phthalocyanine derivative RLP068 is present at the concentration 2 mM in the vehicle Gel 9, the accumulation in the epidermis is 3 times higher than that obtained with the vehicle Gel 7, containing RLP068 1 mM, which in turn leads to a penetration into the epidermis 13 times higher than that obtained with the vehicle Gel 8 (RLP068 0.5 mM).

Figure 10:
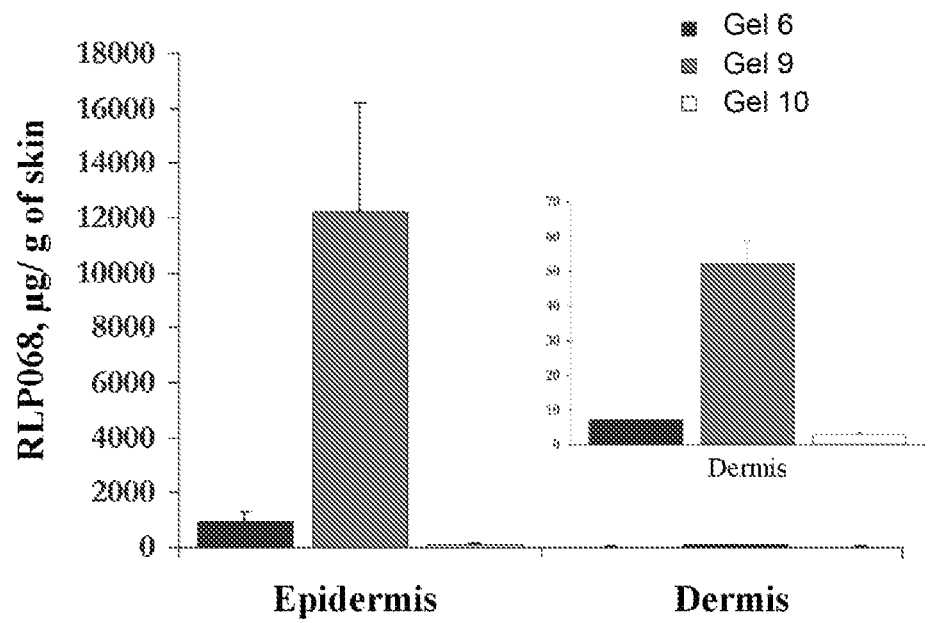

As highlighted in FIG. 10, a decrease in the concentration of TTO in the formulation, switching from 20% in the vehicle Gel 9 to 0.25% in the vehicle Gel 10, leads to a reduced accumulation of photosensitizer in both skin layers, epidermis and dermis. The value obtained is also 8 times lower than the accumulation data in the epidermis for the formulation Gel 6, not containing TTO.

As an alternative to TTO, which in addition to being a good promoter of skin penetration has a significant antimicrobial and antifungal activity, two promoters having no pharmacological activity were tested.

Figure 11:
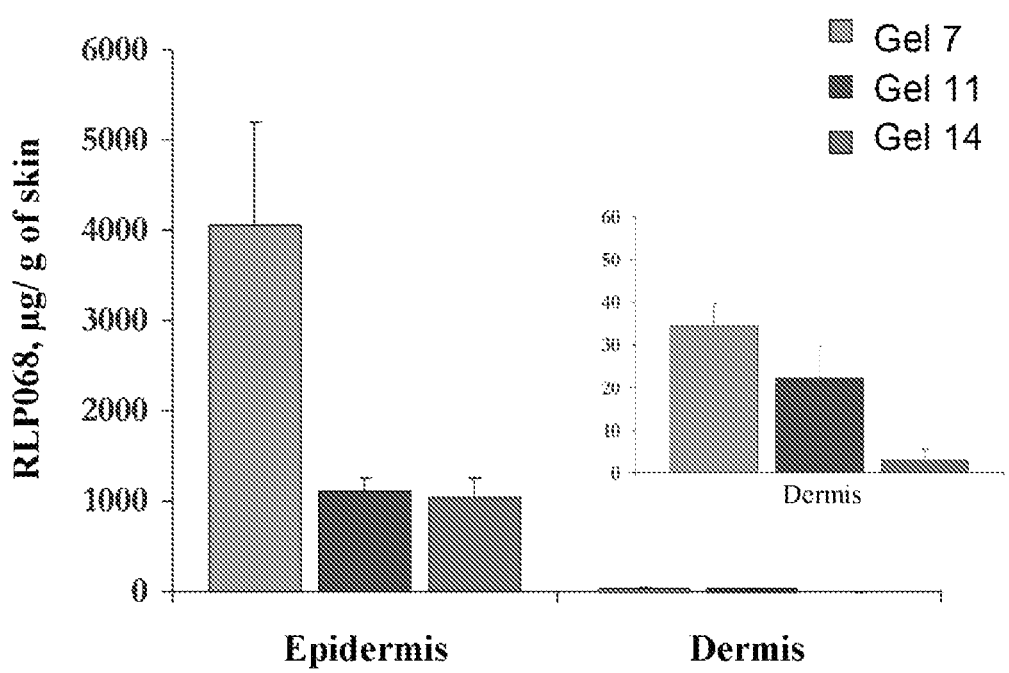

The formulation Gel 7 containing 20% of TTO, was then compared with the formulations Gel 11 and Gel 14, containing 20% of (±)-α-bisabolol (BIS) and 20% of isopropyl myristate (MYR), respectively. As can be seen from the data reported in Table 4 and FIG. 11 there are no statistically significant differences in the amounts of photosensitizer accumulated in the epidermis between the vehicles Gel 11 and Gel 14 and the difference regarding the accumulation data in the dermis is however minimal (22.15±7.59 µg/g for Gel 11 and 10.98±2.68 µg/g for Gel 14).

For both formulations the accumulation of RLP068 compared to that obtained with the vehicle Gel 7 is 4 times lower in the epidermis, while in the dermis it is 1.5 and 3.5 times lower for vehicles Gel 11 and Gel 14 respectively.

By removing EtOH from the formulation Gel 11 and by analysing the results of the skin penetration tests obtained with the corresponding vehicle Gel 13, it is clearly noted that the amount of phthalocyanine accumulated in the skin is reduced by about half in the epidermis, and by about 8 times in the dermis.

Figure 12:
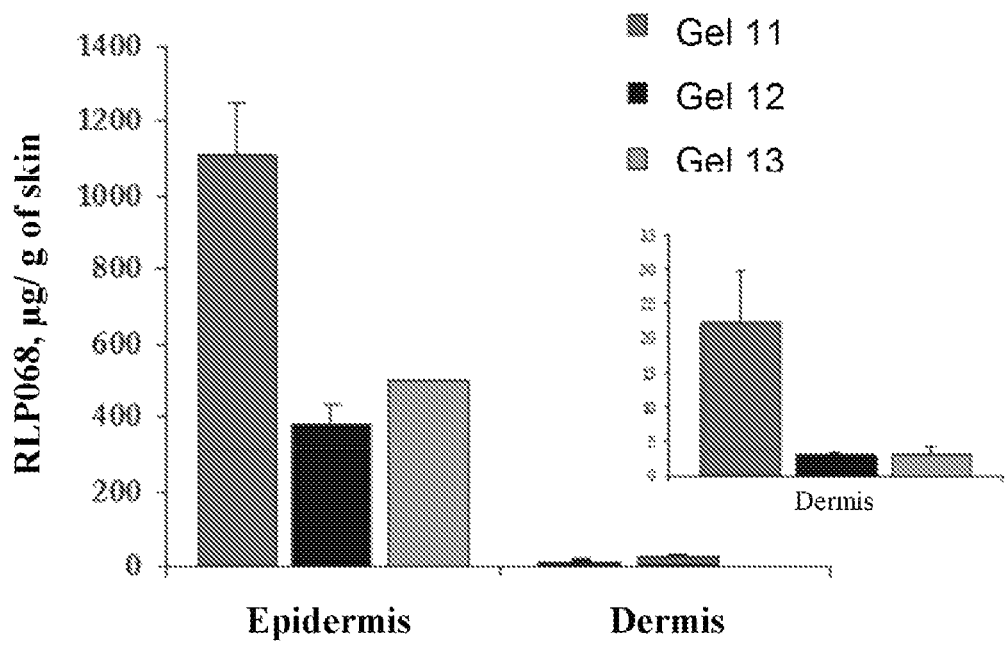

The data obtained, shown in FIG. 12, also confirm in this case that the presence of Ethanol can have a synergistic effect with the permeation promoter. In fact, there is a switch from 503.91±119.62 µg/g of RLP068 accumulated in the epidermis with the vehicle Gel 13, containing only 20% of BIS and from 589.89±328.64 µg/g of RLP068 accumulated with Gel 4, containing only 20% of EtOH, to 1109.01±144.67 µg/g of RLP068 penetrated into the epidermis when EtOH and BIS are present in the same amount in the same formulation (Gel 11).

Figure 13:
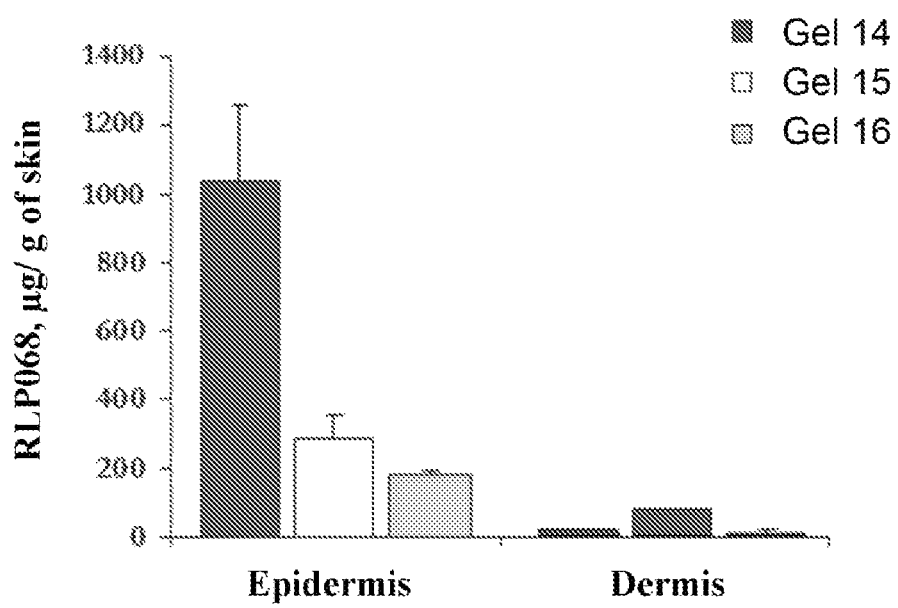

By decreasing the concentration of BIS and MYR from 20% to 6% (vehicles Gel 12 and Gel 15) there is a reduction of about 3 times the amount of photosensitizer accumulated in the epidermis for both formulations; the penetration values in the dermis also decrease, especially for the vehicle Gel 12, wherein the amount of photosensitizer is about 8 times lower. These results, shown graphically in FIGS. 12 and 13, therefore demonstrate the dependence of the promoter action on its concentration.

A formulation containing 6% of MYR without EtOH (Gel 16) was also prepared. Also in this case the synergy action present between EtOH and MYR has been demonstrated; the accumulation values in the epidermis for the formulation Gel 16 are in fact 1.6 times lower than those obtained with the formulation Gel 15 containing 20% of EtOH together with the promoter.

4.2. Human Skin 4.2.1. Transdermal Permeation

Some of the semi-solid vehicles prepared (Table 3) were subjected to transdermal permeation tests through human skin using vertical diffusion cells of the Gummer type.

The following formulations were tested: Gel 3, Gel 7, Gel 11, Gel 14 and Gel 16.

The results of the permeation tests through the human skin highlight that no formulation allowed the permeation of RLP068: in fact, no appreciable amounts of product were detected in the receptor compartment.

4.2.2. Skin Distribution

Mechanical Separation of the Skin Layers

Figure 14:
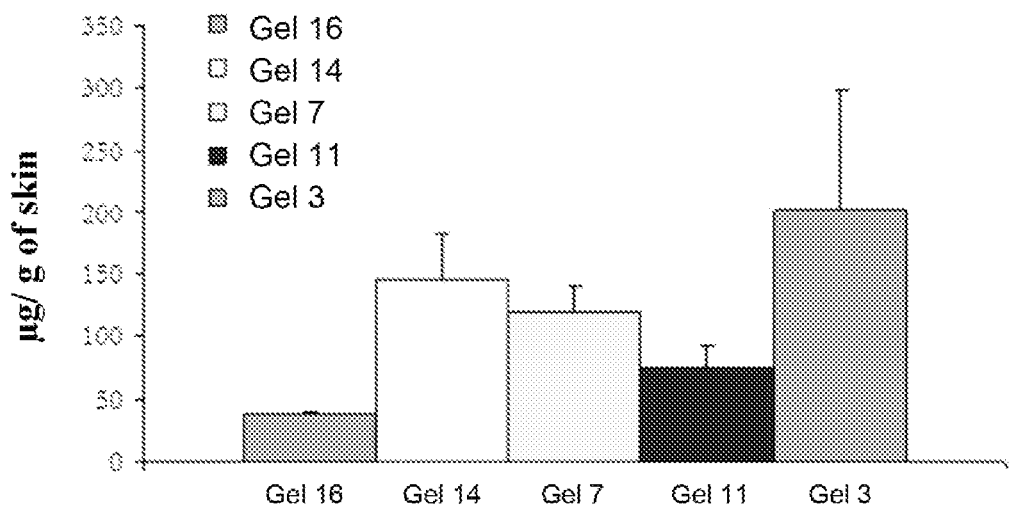
Figure 14:
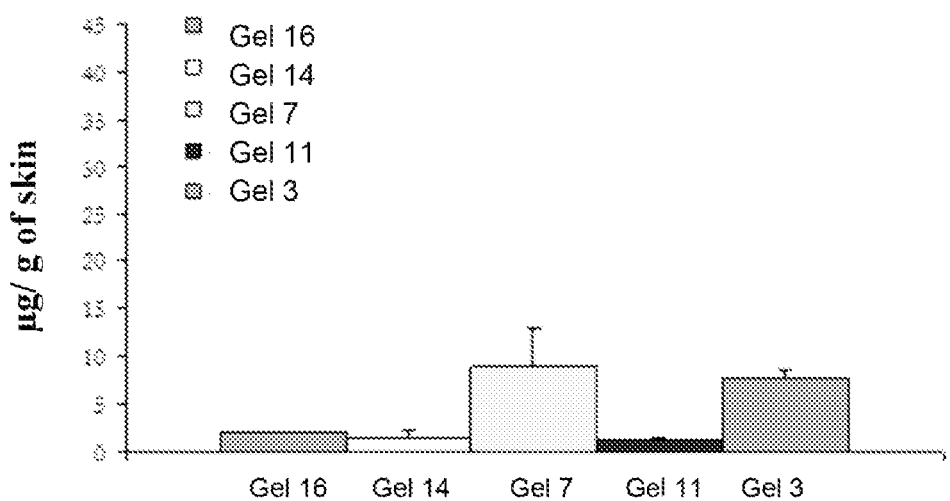

The results of the distribution tests of RLP068 in the skin, obtained following mechanical separation of the skin layers, are summarized in numerical form in Table 5 and graphically in FIG. 14.

TABLE 5

Accumulation of RLP068 in the human skin determined after mechanical separation of the skin layers.

| Vehicle RLP068 | Epidermis µg/g ± SE | Dermis µg/g ± SE |
|---|---|---|
| Gel 3  | 201.10 ± 98.18 | 7.66 ± 0.86 |
| Gel 7  | 120.42 ± 20.66 | 8.98 ± 3.91 |
| Gel 11 | 74.88 ± 17.69  | 1.24 ± 0.19 |
| Gel 14 | 145.26 ± 36.60 | 1.41 ± 0.83 |
| Gel 16 | 38.61 ± 1.24   | 2.10 ± 0.024 |

In all cases the amount of drug accumulated in the skin layers (epidermis and dermis) is reported in µg/g of skin. The data obtained are expressed as a mean of at least three determinations±standard error (SE).

The formulation Gel 3, containing 15% of EtOH in PG and Transcutol®P, showed the highest accumulation of RLP068 in the epidermis, in which 201.10±98.18 µg/g were found. The amount of photosensitizer accumulated in the epidermis is about 26 times higher than that accumulated in the dermis.

When the derivative RLP068 is applied on the skin conveyed in the formulation Gel 7, containing also 20% of EtOH and 20% of TTO in addition to Transcutol®P, the amount of photosensitizer accumulated in the epidermis is 1.7 times lower than that obtained with the formulation Gel 3, while the values relating to the accumulation in the dermis do not significantly differ for the two formulations.

The two formulations containing skin permeation promoters alternative to TTO were also tested on human skin: (±)-α-bisabolol and isopropyl myristate for the formulations Gel 11 and Gel 14, respectively.

The results of the distribution tests have shown that, although there are no statistically significant differences in the values of accumulation in the dermis, the amount of RLP068 accumulated in the epidermis when the vehicle applied on the skin is Gel 14 is about twice that found with the vehicle Gel 11. The amount of drug found in the epidermis with the vehicle Gel 14 is not significantly different from that found when the formulation Gel 7 is applied on the skin.

By applying on the skin the formulation Gel 16, containing 6% of MYR in only Transcutol®P as a solvent, the amount of RLP068 accumulated in the epidermis was 38.61±1.24 µg/g, from 2 to 5 times lower than the accumulation values obtained in the same layer with all the other formulations tested. On the contrary, the amount of drug found in the dermis is of the same order of magnitude obtained with the other vehicles.

The results obtained from the skin distribution tests of RLP068 on human skin were also compared with those obtained using the hairless rat skin as skin model. In all cases the amount of photosensitizer accumulated in the rat epidermis is higher than that found in human skin, with values ranging from 33.6 times higher for Gel 7 to 4.7 for Gel 16. The only exception is the vehicle Gel 3, for which the human skin was instead more permeable, with accumulation values of RLP068 in the epidermis 4.4 times higher than those obtained with the rat skin.

Separation of the Skin Layers by Cryomicrotome

Figure 15:
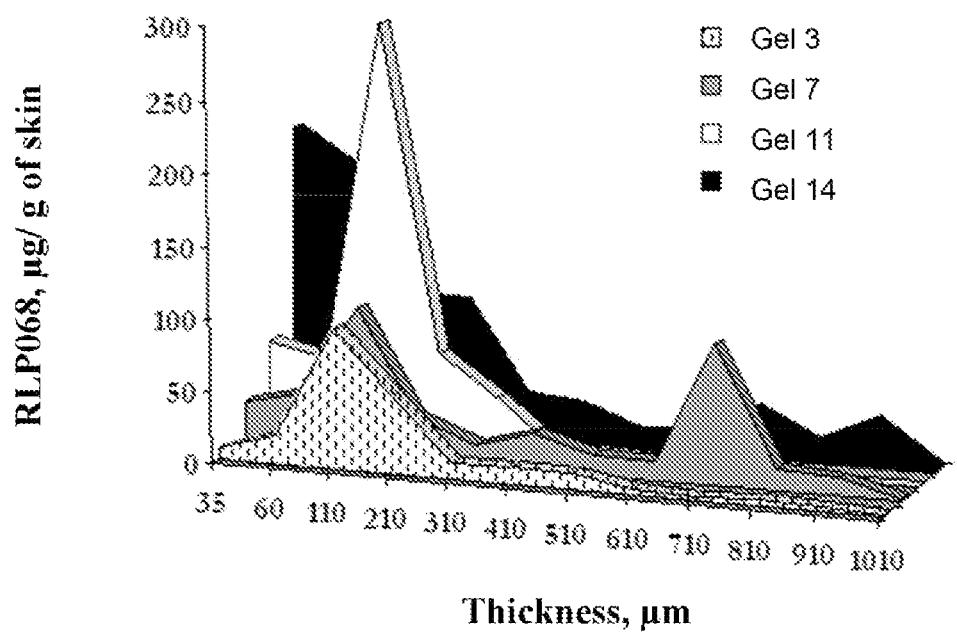

The results of the distribution tests of RLP068 in the skin, obtained following separation of the skin layers by cryomicrotome, are summarized in numerical form in Table 6 and graphically in FIG. 15.

TABLE 6

Distribution of RLP068 (formulations Gel 3, Gel 7, Gel 11 and Gel 14) in human skin after separation of the skin layers by cryomicrotome

| Skin depth (mm) | Gel 3 Accumulated amount (mg/g) ± S.E. | Gel 7 Accumulated amount (mg/g) ± S.E. | Gel 11 Accumulated amount (mg/g) ± S.E. | Gel 14 Accumulated amount (mg/g) ± S.E. |
|---|---|---|---|---|
| 35   | 8.28 ± 0.60   | 32.51 ± 14.78  | 67.06. ± 22.70  | 213.50 ± 52.41 |
| 60   | 20.85 ± 6.94  | 41.51 ± 5.22   | 58.55 ± 38.53   | 187.74 ± 88.57 |
| 110  | 97.56 ± 19.86 | 103.98 ± 8.74  | 296.05 ± 118.06 | 97.58 ± 38.47 |
| 210  | 54.82 ± 20.63 | 31.34 ± 6.47   | 66.75 ± 29.46   | 96.30 ± 38.64 |
| 310  | 11.69 ± 4.31  | 14.35 ± 0.71   | 38.64 ± 17.69   | 30.89 ± 11.63 |
| 410  | 12.62 ± 5.21  | 26.08 ± 22.05  | 5.71 ± 2.35     | 27.78 ± 19.18 |
| 510  | 11.99 ± 0.46  | 14.83 ± 12.12  | 6.77 ± 2.46     | 12.42 ± 2.94 |
| 610  | 4.46 ± 1.23   | 13.96 ± 5.39   | 1.27 ± 0.75     | 17.11 ± 7.94 |
| 710  | 2.02 ± 0.44   | 96.45 ± 29.76  | 2.80 ± 2.80     | 35.78 ±23.30 |
| 810  | 4.53 ± 0.55   | 15.22 ± 13.99  | —               | 15.30 ± 5.60 |
| 910  | 3.12 ± 1.43   | 12.49 ± 6.37   | —               | 33.08 ± 22.14 |
| 1010 | 0.95 ± 0.083  | 2.05 ± 0.57    | —               | 4.17 ± 1.45 |

In all cases the amount of drug accumulated in the skin layers is reported in µg/g of skin. The data obtained are expressed as a mean of at least three determinations±standard error (SE).

When the formulations under examination were applied on the skin, the highest concentration of RLP068 was found in the most superficial sections of the skin, corresponding to the epidermis. In case of the vehicles Gel 7 and Gel 11, the maximum accumulated amount (A.A.) was at 110 µm, with values equal to 103.98±8.74 and 296.05±118.06 µg/g, respectively. For the formulations Gel 3 and Gel 14, the highest accumulation of RLP068 was found at the depths of 110 µm (A.A.=97.56 µg/g) and 35 µm (A.A.=213.50 µg/g), respectively, therefore much more on the surface than the vehicles mentioned above.

In the deepest sections, corresponding to the dermis, the amount of RLP068 was much lower. For the formulation Gel 11 the photosensitizer concentration decreased sharply, it was reduced by 6.5 times, switching from 310 to 410 µm. The same trend was followed by the vehicle Gel 3, with which the amount of RLP068 accumulated in the skin was reduced by 4.5 times switching from 210 to 310 µm. On the contrary, the formulations Gel 7 and Gel 14 showed a gradual decrease in the concentration of photosensitizer in the deepest layers of the skin, with peaks of RLP068 around 30 µg/g at the depths of 710, 910 1010 µm for the formulation Gel 14 and with a single more consistent peak (A.A.=96.45 µg/g) at 710 µm for the formulation Gel 7.

5. Mucoadhesive Capacities

A series of formulations based on RLP068 and containing various hydrophilic polymers were prepared for a preliminary evaluation of the mucoadhesive capacities thereof. Transmucosal permeation and distribution studies of the drug were performed on the same formulations, which provided for the sectioning of the mucosa by cryomicrotomy.

The formulation that proved to be satisfactory when compared with the formulation Gel 3, chosen as a reference, has been the subject of more in-depth studies. Said formulation was used to convey phthalocyanine MRLP164.

5.1. Preparation of Formulations Containing the Derivatives RLP068 and MRLP164 (1.0 mM)

Transcutol® P (Gattefossè) as a solvent, propylene glycol (PG) and EtOH as cosolvents, hydroxypropyl cellulose (HPC, Klucel® HF, Hercules), xanthan gum (XG, Xantural® 75, C.P. Kelco) and polyvinylpyrrolidone (PVP, Kollidon®VA64, Basf) as viscous agents. As a preservative, a mixture of parabens and phenoxyethanol (Fenocombin® 0.2% w/w, Formenti, Milan) was used and tocopherol acetate (0.05% w/w, Sigma) was added as a stabilizer.

All formulations were prepared by first solubilizing at room temperature phthalocyanine and tocopherol acetate (when present) in Transcutol® P. Subsequently the other cosolvents were added, allowing under stirring for about an hour. The final product was obtained by adding the suitable amount of viscous polymer and Fenocombin® (when present) to the solution and allowing to stir until complete and homogeneous dispersion of the viscous polymer.

5.2 Preliminary Study: Formulations Based on RLP068

The composition of the formulations containing RLP068 used for the preliminary evaluation is shown in table 7.

The study envisaged a) the evaluation of the mucoadhesive properties, b) the evaluation of the rheological properties and c) a screening on the effect produced by the formulation in the accumulation of phthalocyanine at the mucosal level.

TABLE 7

Percentage composition (w/w) of the vehicles used for the preliminary tests

| Components (% w/w) | FORMULATIONS | | | | |
|---|---|---|---|---|---|
| | Gel 3 | Gel 17 | Gel 18 | Gel 19 | Gel 20 |
| RLP068 | 0.132 | 0.132 | 0.132 | 0.132 | 0.132 |
| EtOH | 15.00 | 5.00 | — | — | — |
| PG | 49.00 | 49.0 | 20.00 | 20.0 | 49.00 |
| Transcutol ® P | 34.368 | 34.368 | 34.368 | 34.368 | 34.368 |
| HPC | 1.50 | 1.50 | 1.50 | — | 1.50 |
| XG | — | — | — | 1.50 | — |
| PVP | — | — | — | — | 5.00 |
| H₂O | — | 10.0 | 44.00 | 44.0 | 10.0 |

5.3 Evaluation of Formulations Containing RLP068 and MRLP164

The composition of the formulations containing RLP068 and MRLP164 used for the second part of the study is shown in table 8.

The formulations were subjected to rheological analysis both as such and after dilution with artificial saliva in a 1:1 ratio. In addition, the study of permeation and accumulation of phthalocyanine in the buccal mucosa was performed for two treatment times (30 minutes and 5 hours).

TABLE 8

Percentage composition (w/w) of semi-solid vehicles

| Components (% w/w) | Gel 3 | Gel 18 | Gel 21 | Gel 22 |
|---|---|---|---|---|
| RLP068 | 0.132 | 0.132 | | |
| RLP164 | | | 0.132 | 0.132 |
| EtOH | 15.00 | | 15.00 | |
| PG | 49.00 | 20.00 | 49.00 | 20.00 |
| HPC | 1.500 | 1.500 | 1.500 | 1.500 |
| Transcutol ® P | 34.118 | 34.118 | 34.118 | 34.118 |
| H₂O | | 44.00 | | 44.00 |

5.4 Rheological Measurements

In order to characterize the behaviour of the formulations after preparation and after any "in vivo" application on the buccal mucosa, rheological measurements were carried out on the formulations as such and after diluting them with artificial saliva (FS) in a 1:1 ratio.

The rheological behaviour was determined by means of a rotary viscometer (Haake Rheostress RS 150, measuring body plate-cone C60/4).

The composition of the artificial salivary fluid was as follows: $NaHCO_3$ 5.208 g/l, $K_2HPO_4 \cdot 3H_2O$ 1.369 g/l, NaCl 0.877 g/l, KCl 0.477 g/l, $CaCl_2 \cdot 2H_2O$ 0.441 g/l, $NaN_3$ 0.5 g/l, porcine gastric mucin (TCI, Tokyo Kasei, J) 2.160 g/l. All measurements were carried out at a constant temperature of 25° C. for speed gradient values comprised between 0 and 200 $s^{-1}$ and for a duration of 300 s. From the graphs obtained, the correlation between shear stress (τ) and speed gradient (D) was assessed by mathematical processing carried out with the RheoWin Pro software and the apparent viscosity values (η') of the different formulations were calculated for D=10 and 20 $s^{-1}$.

The viscosity values for all the formulations are shown in table 9.

TABLE 9

Viscosity measurements of the formulations under study

| Formulation | Viscosity, Pa · s | |
|---|---|---|
| | D = 10 $s^{-1}$ | D = 20 $s^{-1}$ |
| Gel 3 | 4.22 | 2.53 |
| Gel 17 | 1.83 | 1.14 |
| Gel 18 | 3.58 | 2.15 |
| Gel 19 | 1.15 | 0.68 |
| Gel 20 | 2.22 | 1.44 |
| Gel 21 | 3.57 | 2.13 |
| Gel 22 | 1.62 | 1.05 |
| Gel 3/FS | 0.87 | 0.55 |
| Gel 18/FS | 0.35 | 0.23 |
| Gel 21/FS | 0.29 | 0.22 |
| Gel 22/FS | 0.14 | 0.11 |

The rheological behaviour for all the formulations studied was of the pseudoplastic type both for the formulations as such and after dilution with artificial saliva. Among the formulations containing phthalocyanine RLP068 only Gel 18 showed viscosity values comparable to those of Gel 3.

Dilution with artificial saliva resulted in an evident reduction of viscosity at both speed gradients by 5-10 times for all formulations although the pseudoplastic behaviour was maintained.

5.5 Mucoadhesion Studies

Figure 16:
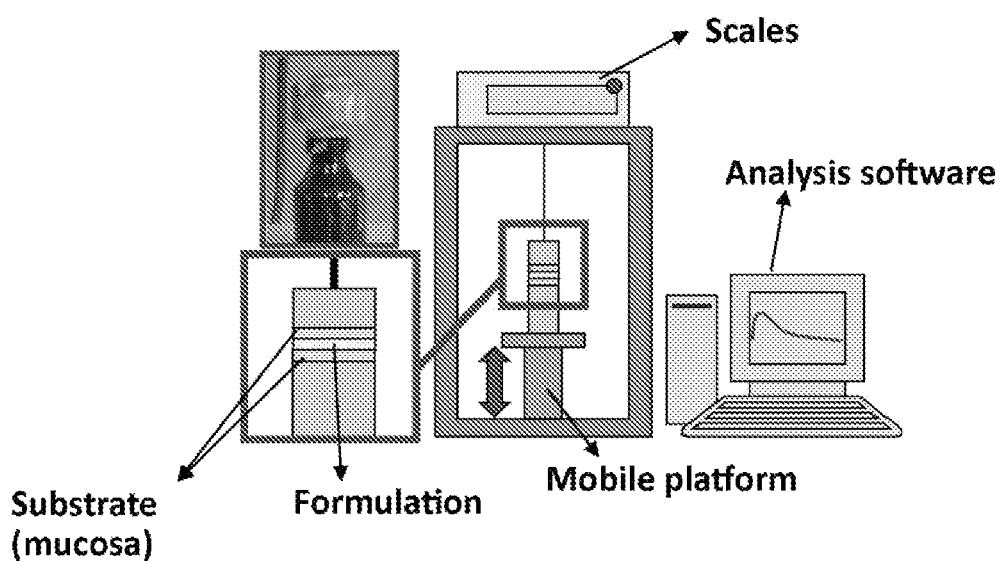

The evaluation of the mucoadhesive properties of the formulations under study was carried out by measuring the work necessary to separate two mucosal surfaces between which the formulation under examination (50 µl) was placed. The mucosal surfaces were made up of porcine buccal mucosa. The equipment used consisted of microscales, a mobile platform and a computerized system capable of registering the force necessary to detach the two surfaces (sample under examination/mucosal layer) as a function of elongation. A scheme is shown in FIG. 16.

Figure 17:
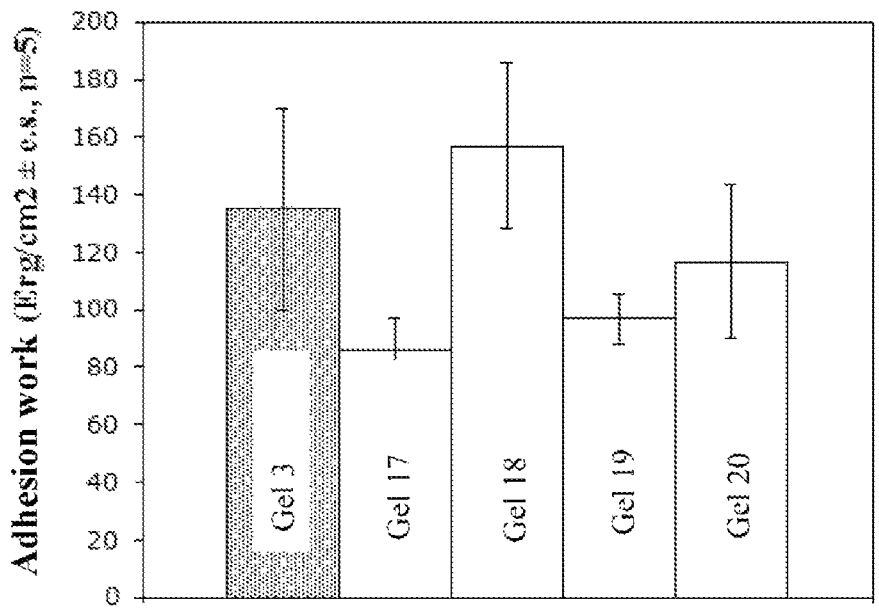

The area under the curve that represents the adhesion work (force×elongation) is calculated from the graphs obtained. The results obtained are shown in FIG. 17.

The best mucoadhesive properties are observed for the formulations Gel 18 and Gel 20, whose values, respectively of 156.98±28.9 and 116.77±26.66 erg/cm$^2$, were comparable to those obtained for the reference Gel 3 (134.95±35.27 erg/cm$^2$).

5.6 Ex Vivo Transmucosal Permeation and Mucosal Distribution Studies

Pig buccal mucosa (cheek) donated by a Research Institute was used for the permeation studies.

The "ex vivo" release studies were performed using the vertical diffusion cell described by Gummer et al. (1987). This cell consists of a receptor compartment having a volume of 5.0 ml and a diffusion area of 3.14 cm$^2$. The receptor solution was stirred with a magnetic stirrer at a constant speed of 600 rpm and the temperature of the receptor compartment was controlled by circulating water thermostated at 37° C. in the double wall of the cell. In the present study, phosphate buffer 66.7 mM, pH=7.4, isotonized with sodium chloride (0.44 g/100 ml), and containing sodium azide (0.003%) as a preservative was used as the receptor phase. The formulations under study were used as the donor phase. In all cases, at suitable time intervals, about 5.0 ml of solution were withdrawn from the receptor compartment, replacing them with an equal volume of fresh buffer. The amount of photosensitizer present in the samples was determined by fluorimetric analysis. The experiments lasted 30 minutes and 5 hours. For each test, 4 replicates were performed. The receptor phase samples were frozen until fluorimetric determination, after adding a suitable amount of aqueous solution of sodium dodecyl sulfate (SDS 4% w/v).

The cryomicrotome separation technique was used to evaluate the amount of photosensitizer distributed within the various layers of mucosa after the permeation tests. The mucosal sectioning procedure was performed at −25° C. with a cryomicrotome (Cryostat mod. Mev Slee Technik GMBH, Mainz, D). The mucosal membrane was stretched and bonded on the special support with the epidermal part facing upwards and was then introduced into the cryomicrotome where, for a few seconds, a slight pressure parallel to the support was exerted thereon by means of a plastic disk. This operation proved to be important for obtaining complete sections of the mucosa, so as to follow the "path" of the phthalocyanine already from the most superficial layers. After freezing, the mucosa was sectioned into 25 µm thick samples and the various sections harvested in previously calibrated vials, putting all the fragments of incomplete slices in the first one, the first complete slice of 25 µm in the second one and so on according to a standardized scheme shown in table 10.

TABLE 10

Example of mucosa harvest after subdivision

| | Number of slices | total µm |
|---|---|---|
| Vial 1 | Incomplete slices | Unknown |
| Vial 2 | 1 | 25 |
| Vial 3 | 2 × 25 | 50 |
| Vial 4 | 4 × 25 | 100 |
| Vial 5 | 8 × 25 | 200 |
| Vial 6 | 8 × 25 | 200 |
| Vial 7 | Residue | Unknown |

Taking into account that presumably the amount of photosensitizer in the sections decreases with the increase of the depth of the mucosa (therefore of the number of sections), in order to obtain an amount of phthalocyanine higher than the sensitivity limit of the analytical method, more sections corresponding to the deepest part of the mucosa were harvested in the same vial.

Finally, the mucosal residue from which it was no longer possible to obtain a complete section was put in the last vial.

The thickness of the incomplete portions and the residue was calculated on the basis of their weight, referring to layers of mucosa of known thickness and weight. Subsequently, each sample was digested by adding suitable amounts (1-10 ml) of aqueous solution of SDS 4% w/v., under stirring for one hour at RT, to extract the photosensitizer therefrom. The change in the volume of the digestive solution has become necessary in order to be able to optimally extract the photosensitizer contained in the biological sample without, by contrast, extremely diluting the solution. Then the suspension was centrifuged for 10 minutes at 10,000 rpm before the analysis.

5.7 Quantitative Determination of Photosensitizers

For both molecules RLP068 and MRLP164 (both with M.W.=1320.5) an aqueous stock solution is prepared in a 10.0 ml volumetric flask, by using an ultrasonic bath, having a concentration of about 1.0 mg/ml (0.76 mM) indicated with S1 (stock solution). For suitable dilution of S1 (100 µl) with aqueous solution of SDS at 4.0%, the standard S2 (0.0152 mM) is prepared in a 5.0 ml volumetric flask. For suitable dilution, a series of standards are obtained starting from S2, the concentration of which, by way of example, is shown in table 11.

TABLE 11

Concentration of SDS solutions used for the construction of the calibration curve

| Standard | Conc. of RLP068 or MRLP164 (µM) |
|---|---|
| S2 | 15.2 |
| S3 | 0.152 |
| S4 | 0.127 |
| S5 | 0.101 |
| S6 | 0.076 |
| S7 | 0.0505 |
| S8 | 0.025 |
| S9 | 0.304 |

For the fluorimetric determination, the standards S3-S9 and a solution consisting of only SDS at 4% w/v were treated as follows, in 1.5 ml eppendorf tubes:

100 μl of standard S3-S9+400 μl of SDS at 4% w/v+500 μl of milliQ water;

500 μl of SDS at 4% w/v+500 μl milliQ water (calibration blank, B1).

Figure 18:
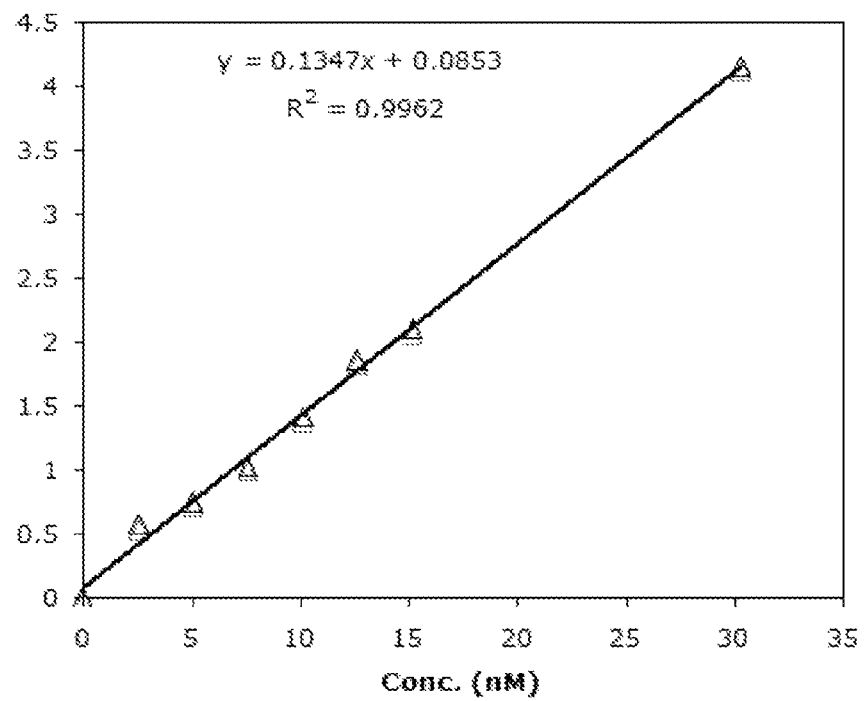
Figure 19:
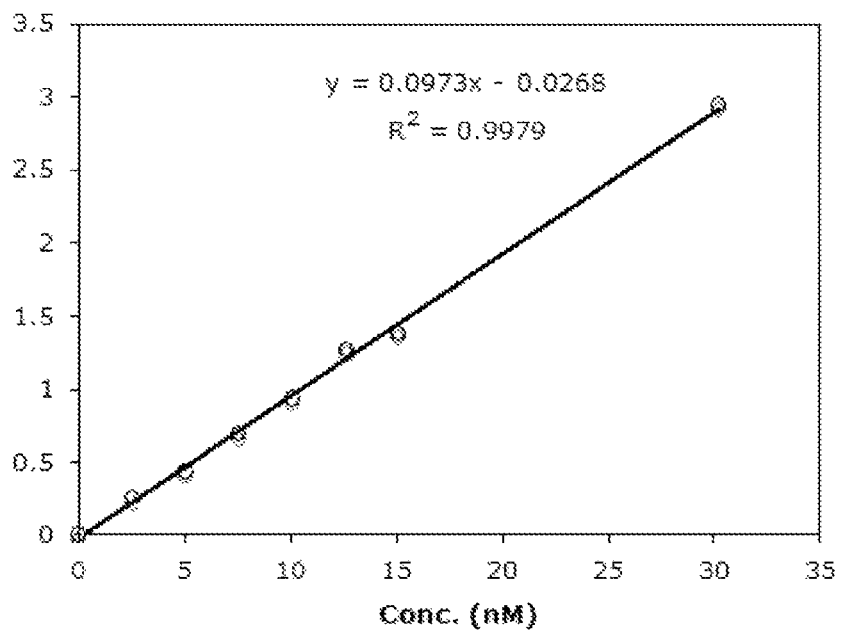

By way of example, FIGS. 18 and 19 show the calibration curves obtained following the procedure described.

For the fluorimetric analysis of phthalocyanines in the samples of the receptor phase coming from the permeation studies, the calibration blank consisted of the same calibration blank (B1) used for the construction of the standard curve.

For the samples coming from the extraction of the mucosa the calibration blank consisted of the supernatant deriving from the treatment of a mucosa sample with 4% SDS diluted in the following way:

500 μl of supernatant+500 μl of milliQ water (calibration blank, B2).

5.8 Analysis of Aqueous Samples Coming from Permeation Studies (Receptor Phase)

The quantitative determination of the photosensitizer present in the receptor phase of the "ex vivo" permeation studies was carried out by diluting 1:1 of the sample withdrawn with a solution of SDS 4% w/v.

5.9 Analysis of Buccal Mucosa Samples

Development of the Extraction Method of the Buccal Mucosa

For the quantitative analysis of phthalocyanines in mucosal samples, sectioned by cryomicrotomy after performing the permeation studies, an extraction method capable of allowing a quantitative recovery of the molecules has been developed:

an exactly weighed mucosa sample (in the range comprised between 2 and 100 mg) was placed in glass vials and added with 10 μl of standard aqueous solution of photosensitizer (concentration variable between 1.0 and 50.0 μM). After 3 hours, variable volumes comprised between 1-20 ml of a solution of SDS 4% w/v were added to the sample which was then stirred with a magnetic stirrer for 1 hour at RT. Subsequently the suspension was centrifuged at 10,000 rpm for 10 minutes and the supernatant analysed with the fluorimeter, after 1:1 dilution with milliQ water. The results of the extraction tests for the two molecules are shown in table 12.

The percentage of phthalocyanine extracted was 66.36 and 66.62% for RPL068 and MRLP164 respectively.

TABLE 12

Development of the extraction method for RLP068 and MRLP164

| Conc. of standard solutions (μM) | Mucosa weight (mg) | Recovery RLP068 (%) | Mucosa weight (mg) | Recovery MRLP164 (%) |
|---|---|---|---|---|
| 10.0 | 6.17 | 66.06 | 75.91 | 69.76 |
| 45.0 | 12.65 | 70.30 | 3.65 | 67.15 |
| 8.5 | 2.31 | 63.24 | 15.58 | 66.74 |
| 50.0 | 91.38 | 69.28 | 83.64 | 63.89 |
| 1.0 | 15.73 | 62.97 | 8.46 | 69.01 |
| 25.0 | 78.06 | 66.31 | 28.07 | 63.18 |

Analysis of the Phthalocyanine in the Buccal Mucosa

The amount of phthalocyanine contained in the different layers of the buccal mucosa was determined after treatment of the samples according to what is reported in Chapter 5.6 and using the solution B2, as a blank for analysis.

5.10 Results

The results of the permeation tests, carried out for 5 hours on the preliminary formulations Gel 17-20 and on the reference Gel 3, containing RLP068, showed that phthalocyanine, under these conditions, was not determinable in the receptor phase indicating that it does not permeate through the buccal mucosa. The distribution studies (FIG. 20) in the layers of the mucosa highlight that a greater accumulation of RLP068 occurred for the formulations Gel 17 and Gel 18, albeit to a lesser extent than that produced by the reference Gel 3.

Figure 20:
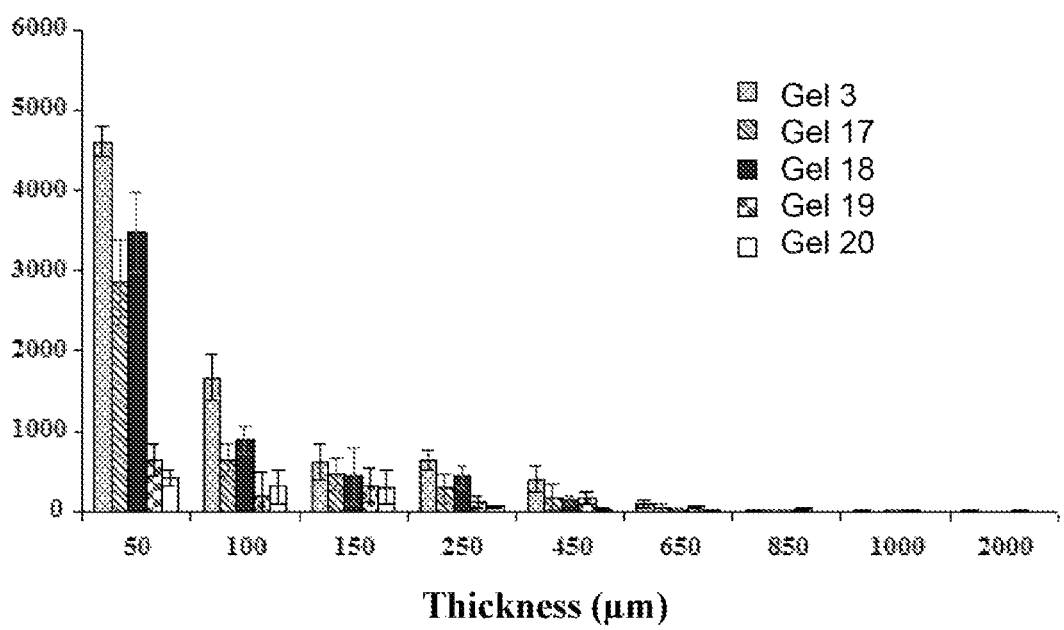
Figure 21:
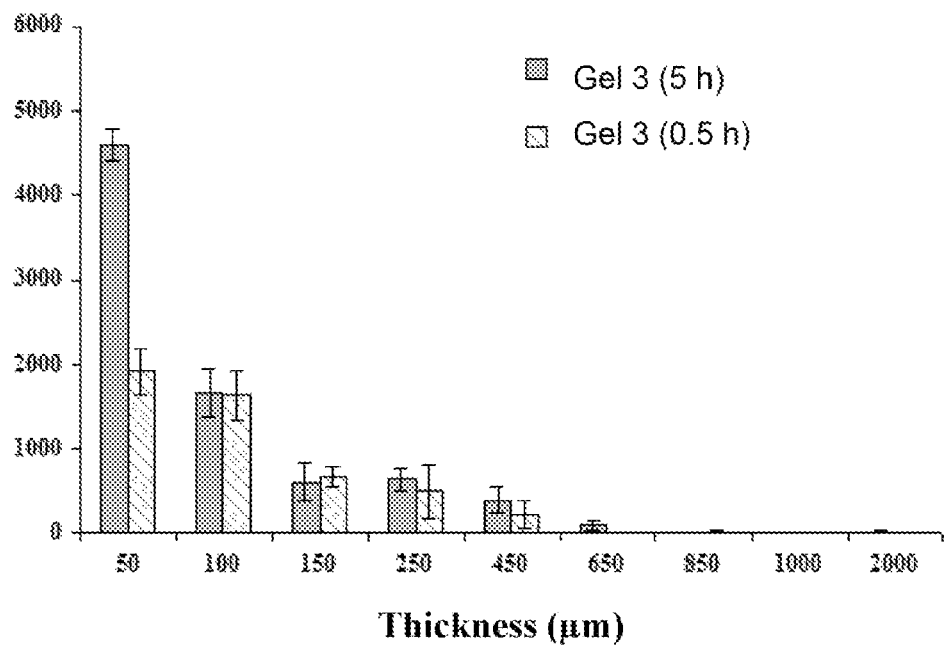
FIG. 21—Distribution of RLP068 in the buccal mucosa after application of the formulation Gel 3 for 5 hours and 30 minutes (Mean±s.e., n=6)
Figure 22:
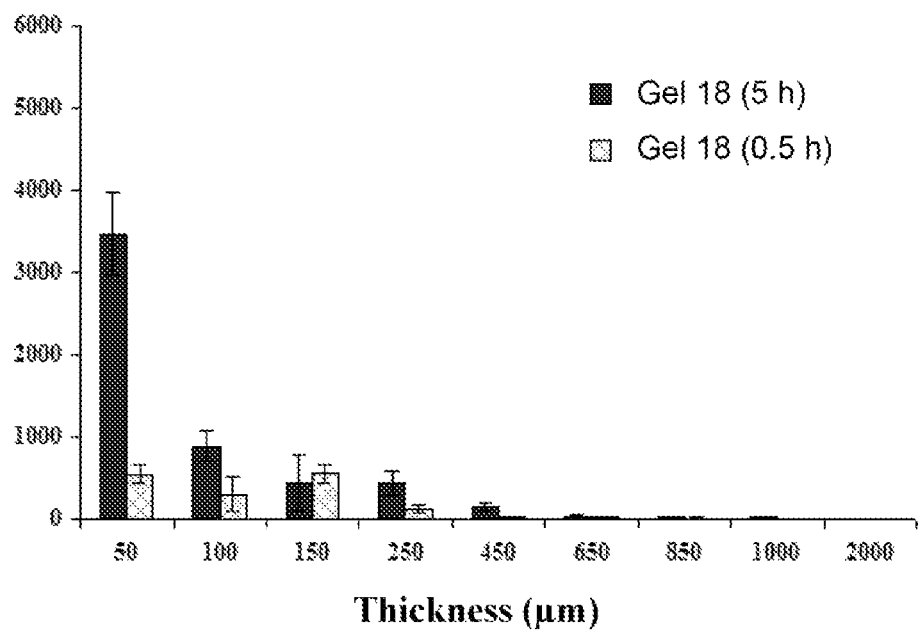
FIG. 22—Distribution of RLP068 in the buccal mucosa after application of the formulation Gel 18 for 5 hours and 30 minutes. (Mean±s.e., n=6).
Figure 23:
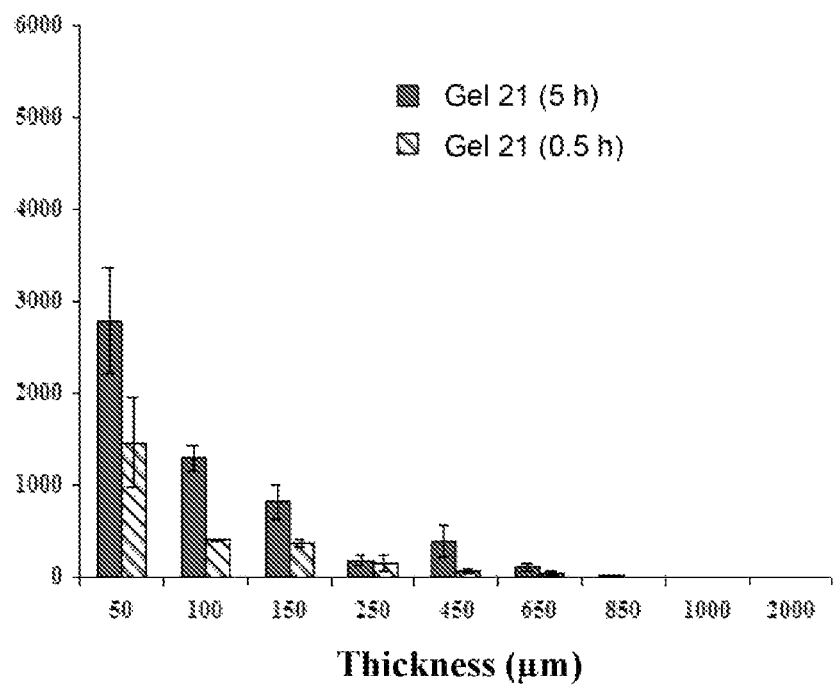
FIG. 23—Distribution of RLP164 in the buccal mucosa after application of the formulation Gel 21 for 5 hours and 30 minutes. (Mean±s.e., n=6)
Figure 24:
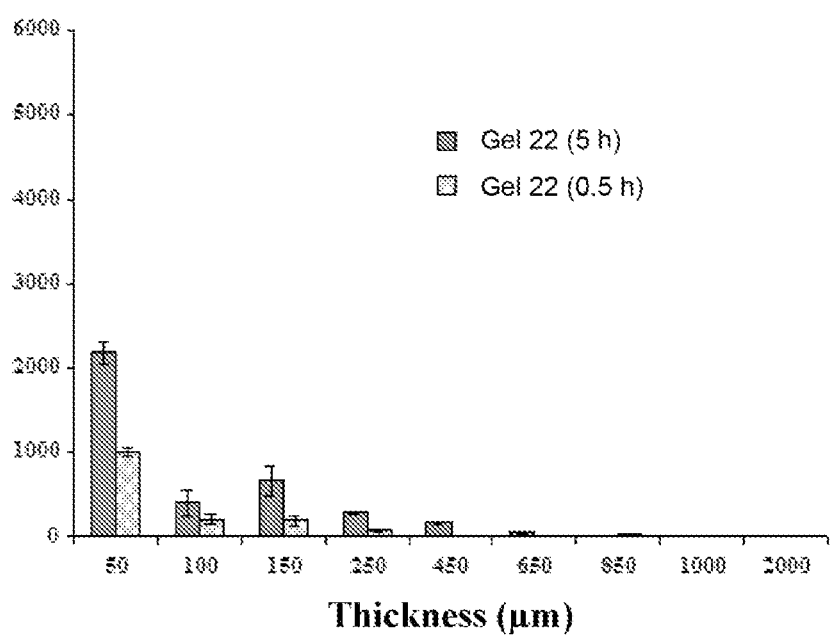
FIG. 24—Distribution of RLP164 in the buccal mucosa after application of the formulation Gel 22 for 5 hours and 30 minutes (Mean±s.e., n=6).
Figure 25:
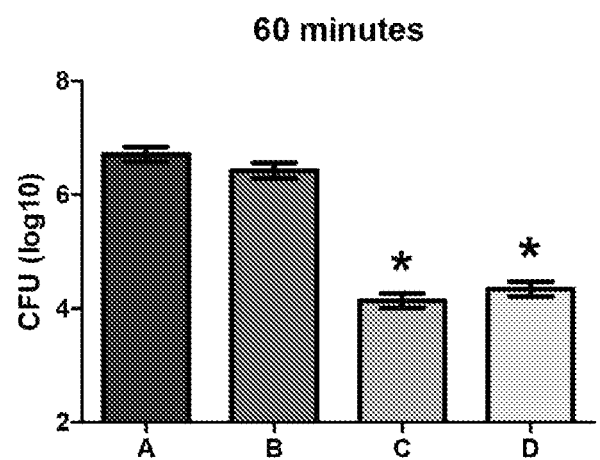
FIG. 25—Efficacy of the APDT treatment with GEL formulation and PLUS formulation according to the invention (time of contact with the lesion: 60 min). Mean and sem estimated from ANOVA analysis (*$p \ll 0.001$)
Figure 26:
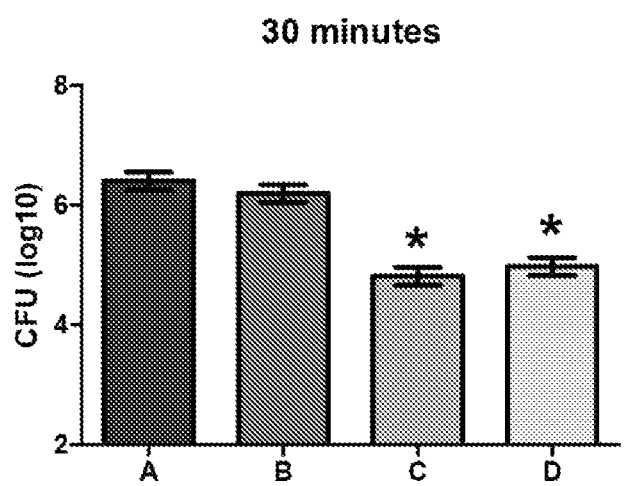
FIG. 26—Efficacy of the APDT treatment with GEL formulation and PLUS formulation according to the invention (time of contact with the lesion: 30 min). Mean and sem estimated from ANOVA analysis (*p<<0.001)

Since preliminary studies highlighted that:

the best mucoadhesive properties were observed for the formulations Gel 18 and Gel 20, the values of which are comparable to those obtained for the reference Gel 3 (see FIG. 17);

a greater accumulation of photosensitizer in the buccal mucosa occurred for the formulations Gel 17 and Gel 18 (see FIG. 20);

only the formulation Gel 18 showed viscosity values comparable to those of Gel 3 (see table 9);

it was decided to test the formulations Gel 3 and Gel 18. These formulations were used as the RLP068 and MRLP164 based formulations in the second part of the permeation and distribution studies through the buccal mucosa.

So, the formulations used for the final part of the study were: Gel 3, Gel 18, Gel 21, Gel 22. In addition, these formulations were subjected to rheological investigation after dilution with artificial saliva (see Chap. 5.4).

In order to verify the possible accumulation of phthalocyanine in the buccal mucosa even after a short period of application, the formulations Gel 3, Gel 18, Gel 21, Gel 22 were subjected to drug permeation/distribution studies for 30 minutes and 5 hours.

From the results obtained, it was possible to conclude that in no case an amount of photosensitizer was determinable in the receptor phase, indicating that the active molecules were unable to permeate from these formulations through the pig buccal mucosa.

The results of the distribution studies of photosensitizers in the mucosa are shown in FIGS. 21-24.

From the results obtained it can be observed that the phthalocyanine RLP068 accumulates in greater amount in the first layers of the mucosa (up to 100 μm) compared to MRLP164 regardless of the formulation used. However, the formulation containing ethanol (Gel 3) is more effective in promoting the penetration of the molecules into the mucosa. This behaviour is also maintained for 30 minutes of treatment, a presumable time of contact for an in vivo application.

Industrial Development

The above mentioned formulation development therefore identified Gel 3 as the most suitable topical formulation for clinical and industrial development with the ultimate aim of use in the patient.

The first industrial prototype developed starting from Gel 3 was a GEL formulation (commercially called VULNO-FAST® gel 0.3%) consisting of

| | | |
|---|---|---|
| (a) | RLP068/Cl | 0.3% w/w |
| (b) | diethylene glycol monoethyl ether | 10.0% w/w |
| (c) | propylene glycol | q.s to 100% w/w |
| (d) | EtOH | 10.0% w/w |
| (e) | hydroxypropyl cellulose (Klucel HF) | 1.5% w/w |

In this formulation, compared to Gel 3, the reduction in the concentration of diethylene glycol monoethyl ether is justified by the fact that the results of stability studies carried out on solutions of RLP068/Cl in various possible excipients have shown that diethylene glycol monoethyl ether used as a solvent of RLP068/Cl is not adequately protective against a thermal stress of the aforesaid molecule. Furthermore, the choice of reducing the concentration of diethylene glycol monoethyl ether in favour of that of propylene glycol, which proved to be the most promising for obtaining a final formulation that is stable from a thermal point of view, was also undertaken in the light of the regulatory indications of the FDA according to which the maximum concentration of diethylene glycol monoethyl ether must be less than 5% for transdermal applications and less than 25% for topical applications and therefore below the concentration of diethylene glycol monoethyl ether of Gel 3 (34.118%)

The aforesaid GEL formulation, however, presented some critical points in the industrialization phase which were overcome with a PLUS technological variation thereof (commercially called VULNOFAST® plus) consisting of:

| (a) | RLP068/Cl | 0.3% w/w |
| (b) | diethylene glycol monoethyl ether | 5.0% w/w |
| (c) | propylene glycol | q.s to 100% w/w |
| (e) | hydroxypropyl cellulose (Klucel JF) | 0.1% w/w |

The first modification made to the GEL formulation was the elimination of the Ethanol component. Due to its high flammability, it was found to be critical in terms of scale up during the use of production plants when manufacturing the industrial batches. Furthermore, due to its volatility, the elimination of this component was found to be a guarantee to prevent any sealing problems of the primary packaging. Regarding the viscosity of the formulation, it should be emphasized that the high viscosity value of the GEL formulation, conferred by the high concentration of viscosifier, led in the industrialization phase to the need to use a combination of sterilization techniques to satisfy the sterility requirements of the final product. The formulation was in fact made under aseptic conditions (compounding in asepsis); these operations, carried out manually in a positive pressure isolator, consist in mixing aseptically portions of the semi-finished product subjected to different sterilization techniques. This operating method was deemed impractical in view of a subsequent industrial scale-up of the product towards larger batches, above all due to the high economic impact on the final price of the product.

The PLUS variant features a formulation with a reduction in the thickener content equal to 1:15 which allowed to sterilize the final product with a single technique, that is the sterilizing filtration. This variation in the quantitative composition of the thickener led to a more streamlined process that was easier to control in relation to the microbiological characteristics.

In addition, the manufacturing process adopted for the PLUS variant resulted in a reduction in the sterilization techniques of the primary packaging materials and the automation of the aseptic filling operations, with minimal intervention by operators. The transition to the PLUS variant allowed to increase the manufacturing scale of the device from only 2 kg of formulation for the GEL formulation (VULNOFAST® gel) up to 300-400 kg for the PLUS variant (VULNOFAST® plus) ensuring a marked increase in the batch size of industrial batches.

The PLUS variant was compared with the GEL formulation in the following in vivo efficacy study in the mouse.

The efficacy of PDT treatment with the photosensitizer RLP068/Cl formulated in the two variants (GEL and PLUS) against species of *Staphylococcus* was evaluated in a mouse model of wound infection.

Male mice of the BALB/c strain were used throughout the study. A methicillin-resistant clinical isolate of *Staphylococcus aureus* was used for experimental infection (ATCC 43300 strain supplied by the Infectious Diseases Department of the *Ospedali riuniti* [Torrette section] of Ancona, Italy). The bacterial colonies were harvested after 18 hours of growth on heart-brain agar (BHI) and suspended in physiological solution to obtain a final inoculation of $1 \times 10^8$ cells/mi.

On day 0, the mice were anesthetized and the hair in the back area was shaved; the skin was then cleaned with 10% povidone-iodine solution. Using a 0.7 mm diameter template, a wound was produced on each animal that crossed the *Panniculus carnosus* in the subcutaneous layer of the skin of the back. An adhesive gauze pad was placed on each wound, subsequently inoculated with 100 µl of bacterial suspension. The pocket was closed with suture clips. This procedure gives rise to a local abscess that develops after 24-48 h.

After 48 h (day +2), i.e. when the bacteria multiplied inside the wound and created an infection, the wounds were opened, the gauze was removed and PDT treatment with the photosensitizer RLP068/Cl was started.

The treatment groups are summarized below:
Group A Infection control (no treatment)
Group B Light control (illumination with LED source at 630 nm)
Group C APDT treatment with GEL formulation 0.3%+ LED source at 630 nm
Group D APDT treatment with PLUS variant 0.3%+LED source at 630 nm The means refer to 2 independent experiments with n=8 per experimental group.

The final processing has n=13-15 per group.

Results:
A single treatment with PDT based on RLP068/Cl formulated in two variants (GEL and PLUS) was very effective at a concentration equal to 0.3% w/w and the bacterial load was substantially reduced compared to the untreated controls with a time of contact with the lesion both of 60 minutes and of 30 minutes.

The PDT treatment based on RLP068/Cl, formulated in two variants (GEL and PLUS) was also significantly different from the group of treatment with the light only (group B); in fact, the light alone was not able to reduce the microbial load.

The results of this non-clinical experimental study conducted on an "ulcer-like" translational model in the mouse therefore allowed to support the bioequivalence, in terms of efficacy as well as tolerability, of the two formulations GEL and PLUS according to the present invention.

The invention claimed is:

1. A topical formulation comprising:
   (a) a Zn-phthalocyanine derivative as a photosensitizing agent;
   (b) diethylene glycol monoalkyl ether as a cutaneous permeation promoter contained in amounts of 3-35% w/w,
   (c) a solvent selected from the group consisting of propylene glycol and polyethylene glycol;
   (d) optionally a cutaneous permeation co-promoter selected from the group consisting of EtOH and iPrOH;
   (e) a viscous agent selected from the group consisting of hydroxypropyl cellulose (HPC), hydroxymethylpropylcellulose (HMPC), polyvinyl alcohol (PVA), carboxymethylcellulose (CMC);

wherein said Zn-phthalocyanine derivative (a) is of formula (I)

(I)

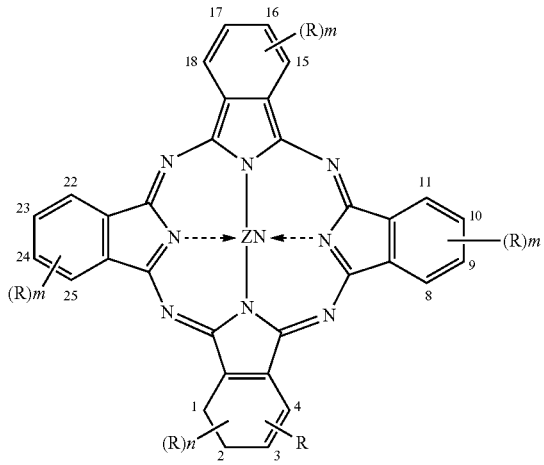

wherein n=0,1 and m=0,1,2 where when n=0 then m=0,1; when n=1 then m=0,2;

R is

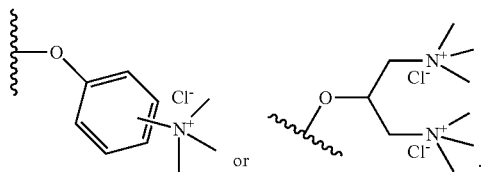

2. The composition according to claim 1, in the form of a non-aqueous transparent gel.

3. The composition according to claim 1, characterized in that it is free of preservatives, stabilizers and other permeation promoters including in particular Tea Tree Oil (TTO), (±)-α-bisabolol (BIS) and isopropyl myristate (MYR).

4. The composition according to claim 1, having a viscosity between 25 and 190000 cP.

5. The composition according to claim 1, in which the photosensitizer (a) is contained in amounts 0.050-0.500% w/w;

the diethylene glycol monoalkyl ether (b) is contained in amounts of 3-35% w/w;

the solvent (c) is contained in sufficient amounts to complete the 100% w/w composition;

the co-promoter (d) is contained in amounts 0-15% w/w;

the viscous agent (e) is contained in amounts 0.05-3% w/w.

6. The composition according to claim 1, wherein the photosensitizer (a) is a compound of formula (I) wherein:

n=0, m=0 and

R, in position 1 or 2, is

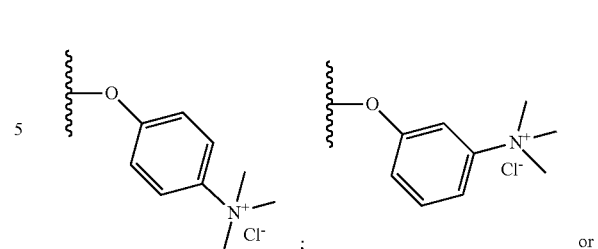

or n=1, m=0 and

R, in positions 1,4 or 2,3, is

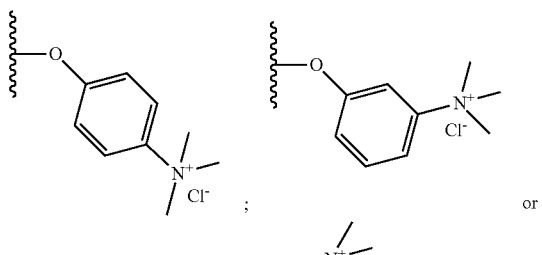

or n=0, m=1 and

R, in positions 1,8 (11),15 (18),22 (25) or 2,9 (10) 16 (17),23 (24), is

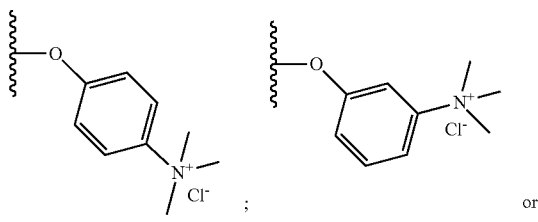

or n=1, m=2 and

R, in positions 2,3,9,10,16,17,23,24, is

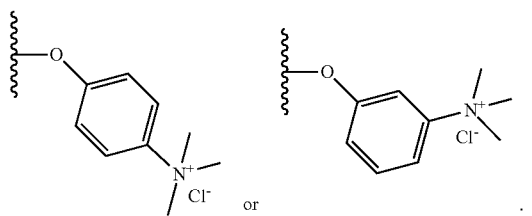 [SMILES: *Oc1ccc([N+](C)(C)C)cc1 ; [Cl-] ; "or" ; *Oc1cccc([N+](C)(C)C)c1 ; [Cl-] ; ";"]

7. The composition according to claim 1, wherein the photosensitizer (a) is the compound 1,8 (11), 15 (18),22 (25)-Tetrakis [3-(N,N,N-trimethylammonium) phenoxy] zinc phthalocyaninate (II) tetrachloride (RLP068/C1).

8. The composition according to claim 7 consisting of:

| (a) | RLP068/Cl | 0.1-0.3% w/w |
|---|---|---|
| (b) | diethylene glycol monoethyl ether | 5.0-10.0% w/w |
| (c) | propylene glycol | q.s to 100% w/w |
| (d) | EtOH | 0-10.0% w/w |
| (e) | hydroxypropyl cellulose | 0.1-1.5% w/w |

9. A method for photodynamic therapy of skin or mucosal affections and for the simulation of repair and scarring process, said method comprising administering the composition according to claim 1 to a subject in need thereof.

10. The method according to claim 9 a simultaneous irradiation with a red light, for the localized topical treatment of skin infections of microbial origin from Gram (+), Gram (−) pathogens, yeasts, fungi and protozoa.

11. The composition according to claim 4, wherein the viscosity is 25-65 cP.

12. The composition according to claim 4, wherein the viscosity is 50000-190000 cP.

* * * * *